US012646617B2

(12) United States Patent
Muhsin et al.

(10) Patent No.: US 12,646,617 B2
(45) Date of Patent: *Jun. 2, 2026

(54) ALARM NOTIFICATION SYSTEM

(71) Applicant: Masimo Corporation, Irvine, CA (US)

(72) Inventors: Bilal Muhsin, San Clemente, CA (US); Emil Sultanov, Anaheim, CA (US); Stephen Quong, Huntington Beach, CA (US)

(73) Assignee: Maismo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/020,852

(22) Filed: Jan. 14, 2025

(65) Prior Publication Data

US 2025/0157645 A1 May 15, 2025

Related U.S. Application Data

(63) Continuation of application No. 18/651,438, filed on Apr. 30, 2024, now Pat. No. 12,230,396, which is a
(Continued)

(51) Int. Cl.
*G16H 40/67* (2018.01)
*G16H 10/60* (2018.01)
(Continued)

(52) U.S. Cl.
CPC ............. *G16H 40/67* (2018.01); *G16H 10/60* (2018.01); *G16H 50/30* (2018.01); *G16Z 99/00* (2019.02); *G16H 40/20* (2018.01)

(58) Field of Classification Search
CPC ........ G16H 40/67; G16H 40/63; G16H 40/20; A61B 2560/0271
See application file for complete search history.

(56) References Cited

U.S. PATENT DOCUMENTS

| | | | |
|---|---|---|---|
| 5,752,976 | A | 5/1998 | Duffin et al. |
| 10,169,607 | B1 | 1/2019 | Sheth |

(Continued)

OTHER PUBLICATIONS

U.S. Pat. No. 9,749,232, Intelligent Medical Network Edge Router, Aug. 29, 2017.
(Continued)

*Primary Examiner* — Joseph D Burgess
(74) *Attorney, Agent, or Firm* — Knobbe, Martens, Olson & Bear, LLP

(57) ABSTRACT

An alarm notification system can enable a clinician to respond to an alarm notification received via a computing device, which may have more advanced functionality than a pager. The clinician's device can include a notification client which can respond to alarm notifications. The notification client can also provide one or more user interfaces that enable the clinician to view information about an alarm, such as information about a patient's status, physiological parameter values, trend data, audio/video of the patient, combinations of the same, or the like. Further, the notification client can provide functionality for a clinician to respond to an alarm, annotate an alarm, and/or indicate that the clinician can or cannot respond to the alarm, among other features. In addition, the clinician device can also (or instead) include an admit module that provides for automatic association of a patient to a device or location.

18 Claims, 28 Drawing Sheets

Related U.S. Application Data continuation of application No. 18/323,001, filed on May 24, 2023, now Pat. No. 12,009,098, which is a continuation of application No. 17/952,793, filed on Sep. 26, 2022, now Pat. No. 11,699,526, which is a continuation of application No. 17/035,382, filed on Sep. 28, 2020, now Pat. No. 11,488,711, which is a continuation of application No. 14/511,972, filed on Oct. 10, 2014, now Pat. No. 10,832,818.

(60) Provisional application No. 61/890,076, filed on Oct. 11, 2013.

(51) Int. Cl.
   *G16H 50/30* (2018.01)
   *G16Z 99/00* (2019.01)
   *G16H 40/20* (2018.01)

(56) References Cited

U.S. PATENT DOCUMENTS

| | | | |
|---|---|---|---|
| 10,825,568 | B2 | 11/2020 | Muhsin et al. |
| 10,832,818 | B2 | 11/2020 | Muhsin et al. |
| 11,488,711 | B2 | 11/2022 | Muhsin et al. |
| 11,699,526 | B2 | 7/2023 | Muhsin et al. |
| D1,022,729 | S | 4/2024 | Forrest et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,009,098 | B2 | 6/2024 | Muhsin et al. |
| 12,014,328 | B2 | 6/2024 | Wachman et al. |
| D1,036,293 | S | 7/2024 | Al-Ali et al. |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Al-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,230,396 | B2 | 2/2025 | Muhsin et al. |
| 12,235,941 | B2 | 2/2025 | Kiani et al. |
| 12,236,767 | B2 | 2/2025 | Muhsin |
| D1,066,244 | S | 3/2025 | Lim et al. |
| D1,066,672 | S | 3/2025 | Al-Ali et al. |
| 2004/0172222 | A1* | 9/2004 | Simpson ............... G08B 21/02 |
| | | | 702/189 |
| 2010/0088120 | A1 | 4/2010 | Gonzalvo |
| 2011/0140896 | A1 | 6/2011 | Menzel |
| 2011/0245707 | A1 | 10/2011 | Castle et al. |
| 2013/0305164 | A1* | 11/2013 | Karunamuni ........ G06Q 10/107 |
| | | | 715/752 |
| 2016/0210430 | A1 | 7/2016 | Saleh |
| 2016/0361026 | A1 | 12/2016 | Sarkar et al. |
| 2017/0287300 | A1 | 10/2017 | Herbst et al. |
| 2024/0180456 | A1 | 6/2024 | Al-Ali |
| 2024/0188872 | A1 | 6/2024 | Al-Ali et al. |
| 2024/0245855 | A1 | 7/2024 | Vo et al. |
| 2024/0260894 | A1 | 8/2024 | Olsen |
| 2024/0267698 | A1 | 8/2024 | Telfort et al. |
| 2024/0277233 | A1 | 8/2024 | Al-Ali |
| 2024/0277280 | A1 | 8/2024 | Al-Ali |
| 2024/0298920 | A1 | 9/2024 | Fernkvist et al. |
| 2024/0306985 | A1 | 9/2024 | Vo et al. |
| 2024/0324953 | A1 | 10/2024 | Telfort |
| 2024/0380246 | A1 | 11/2024 | Moran |
| 2024/0380247 | A1 | 11/2024 | Moran |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |

OTHER PUBLICATIONS

U.S. Pat. No. 10,833,983, Intelligent Medical Escalation Process, Nov. 10, 2020.
U.S. Pat. No. 11,887,728, Intelligent Medical Escalation Process, Jan. 30, 2024.
U.S. Pat. No. 10,832,818, Alarm Notification System, Nov. 10, 2020.
U.S. Pat. No. 11,488,711, Alarm Notification System, Nov. 1, 2022.
U.S. Pat. No. 11,699,526, Alarm Notification System, Jul. 11, 2023.
U.S. Pat. No. 12,009,098, Alarm Notification System, Jun. 11, 2024.
U.S. Pat. No. 12,230,396, Alarm Notification System, Feb. 18, 2025.
U.S. Pat. No. 10,825,568, Alarm Notification System, Nov. 3, 2020.
U.S. Pat. No. 10,667,764, Mobile Patient Alarm Display, Jun. 2, 2020.
U.S. Pat. No. 11,109,818, Mobile Patient Alarm Display, Sep. 7, 2021.
U.S. Pat. No. 11,844,634, Mobile Patient Alarm Display, Dec. 19, 2023.
U.S. Pat. No. 12,193,849, Mobile Patient Alarm Display, Jan. 14, 2025.
U.S. Appl. No. 18/530,852, Intelligent Medical Escalation Process, filed Dec. 6, 2023.
U.S. Appl. No. 18/963,166, Mobile Patient Alarm Display, filed Nov. 27, 2024.

* cited by examiner

MULTI-FACTOR ALARM ESCALATION PROCESS

PATIENT DEVICE/LOCATION ADMIT PROCESS

1900

2110 admit patient

| | |
|---|---|
| last name | Galt 🔍 |
| first name | John |
| middle name | R |
| primary assignment | -- 🔍 |
| secondary assignment | -- 🔍 |

| | |
|---|---|
| label | jgalt |
| room | 101 |
| notes | |

Admit  ←—2510

FIG. 25

VITAL SIGNS VERIFICATION PROCESS

2800

START

2812

RECEIVE USER REQUEST TO CAPTURE AND SUBMIT VITAL SIGNS

2814

CAPTURE MONITORED VITAL SIGN VALUES

2816

OUTPUT CAPTURED VITAL SIGN VALUES FOR CLINICIAN VERIFICATION

2818

RECEIVE ANY MANUALLY-ENTERED VITAL SIGNS

2820

UPON CLINICIAN INSTRUCTION, SUBMIT VITAL SIGNS OVER A NETWORK

END

ALARM NOTIFICATION SYSTEM

RELATED APPLICATION

This application is a continuation of U.S. application Ser. No. 18/651,438, filed Apr. 30, 2024, which is a continuation of U.S. application Ser. No. 18/323,001, filed May 24, 2023, which is a continuation of U.S. application Ser. No. 17/952, 793, filed Sep. 26, 2022, which is a continuation of U.S. application Ser. No. 17/035,382, filed Sep. 28, 2020, which is a continuation of U.S. application Ser. No. 14/511,972, filed Oct. 10, 2014, which application is non-provisional of U.S. Application No. 61/890,076, filed Oct. 11, 2013, the disclosure of which is hereby incorporated by reference in its entirety. Any and all applications, if any, for which a foreign or domestic priority claim is identified in the Application Data Sheet of the present application are hereby incorporated by reference under 37 CFR 1.57.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, $SpO_2$ level, pulse, and blood pressure, among others. Clinicians, including doctors, nurses, physician's assistants, and other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as $SpO_2$ and pulse rate in addition to advanced parameters, such as HbCO, HbMet and total hemoglobin (Hbt, THb, or SpHb) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, CA (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index, signal quality, HbCO, and HbMet among other parameters are also available from Masimo Corporation, Irvine, CA (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt or SpHb), as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366, 208, filed Mar. 1, 2006, titled Noninvasive Multi-Parameter Patient Monitor, which are each hereby incorporated by reference herein in their entirety. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index (PI), signal quality (SiQ), pulse variability index (PVI), HbCO and HbMet among other parameters are also available from Masimo.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

An alarm notification system can enable a clinician to respond to an alarm notification received via a computing device, which may have more advanced functionality than a pager. The clinician's device can include a notification client which can respond to alarm notifications. The notification client can also provide one or more user interfaces that enable the clinician to view information about an alarm, such as information about a patient's status, physiological parameter values, trend data, audio/video of the patient, combinations of the same, or the like. Further, the notification client can provide functionality for a clinician to respond to an alarm, annotate an alarm, and/or indicate that the clinician can or cannot respond to the alarm, among other features. In addition, the clinician device can also (or instead) include an admit module that provides for automatic association of a patient to a device or location.

Once a patient has been admitted (or optionally after), vital signs can be captured by the patient device and/or by the clinician and submitted via the patient device for inclusion in the patient's electronic medical record.

BRIEF DESCRIPTION OF THE DRAWINGS

Throughout the drawings, reference numbers are re-used to indicate correspondence between referenced elements. The drawings are provided to illustrate embodiments of the inventions described herein and not to limit the scope thereof.

FIG. 4 depicts an embodiment of a multi-factor alarm escalation process.

FIGS. 22 through 25 depict example monitoring device user interfaces for admitting a patient to the device.

DETAILED DESCRIPTION

I. Introduction

Figure 1:
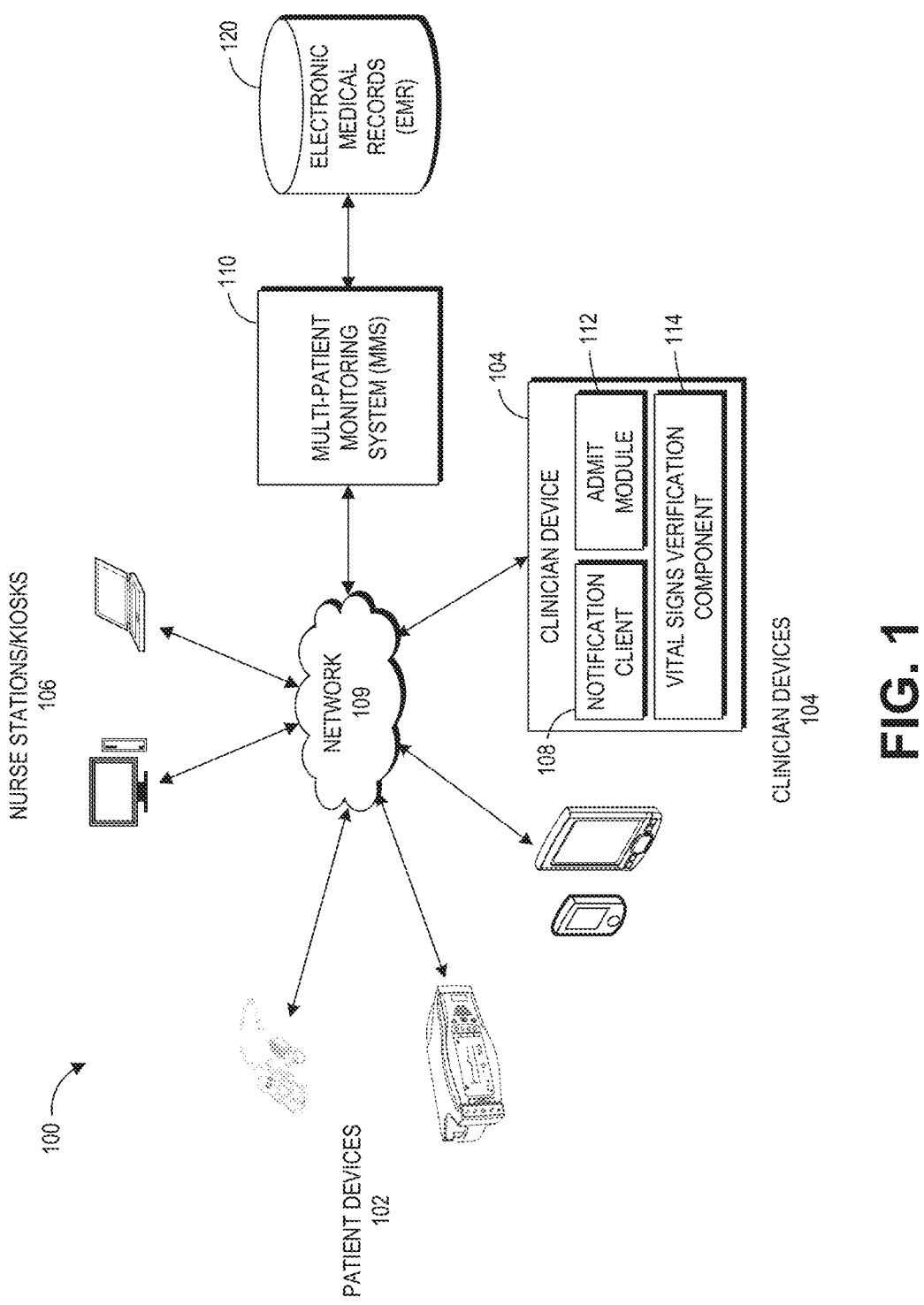
FIG. 1 depicts an embodiment of a clinical computing environment that includes a multi-patient monitoring system.

Patient monitors typically monitor patients' physiological parameters to determine whether the parameters are within safe limits. If a physiological parameter exceeds a safety limit or threshold, or is otherwise trending toward a dangerous condition, a patient monitor can generate an alarm. The alarm may have audible and/or visual characteristics. Typically, the patient monitor sounds an alarm to attract the attention of nearby clinicians to alert the clinicians that the patient may need medical attention. Clinicians within earshot can respond to the patient and clear the alarm. In addition, some patient monitors send alarms over a network to a computer system at a nurse's station to alert the clinicians at the nurse's station. Still other patient monitors send alarms over a network to a paging system, which in turn pages clinicians regarding the alarm. As a result, clinicians who are not within earshot of the audible alarm can still be alerted to the alarm condition and provide a response.

A typical pager system includes a paging appliance or server that receives a notification from a patient device of an alarm condition and forwards a simple alarm message to one or more clinicians' pagers. The alarm message may include information about the patient's name or room number and possibly limited information about the alarm itself (such as "low SpO$_2$"). Pagers used in hospitals and other clinical facilities are typical one way, unidirectional devices and therefore do not provide functionality for clinicians to respond to a page using the pager device itself. Accordingly, a pager system cannot tell if a clinician is going to respond to the alarm. The pager system may instead monitor whether the alarm has been cleared, and after the alarm has not been cleared for a certain amount of time, escalate the alarm to a second clinician (or group of clinicians). During the time when the pager system is waiting to see if the alarm has been cleared, patients may worsen and suffer adverse health effects. Accordingly, pager systems are limited in their capacity to improve patient care outcomes.

This disclosure describes embodiments of alarm notification systems that can enable a clinician to respond to an alarm notification received via a computing device, which may have more advanced functionality than a pager. The clinician device may be, for instance, a cellphone or smartphone, tablet, laptop, personal digital assistant (PDA), or the like. In certain embodiments, the clinician's device includes a notification client which may be a mobile software application, web application, or the like that can respond to alarm notifications. The notification client can also provide one or more user interfaces that enable the clinician to view information about an alarm, such as information about a patient's status, physiological parameter values, trend data, video of the patient, combinations of the same, or the like. Further, the notification client can provide functionality for a clinician to respond to an alarm, annotate an alarm, and/or indicate that the clinician can or cannot respond to the alarm, among other features. Advantageously, in certain embodiments, the notification client can enable a clinician to respond and indicate his or her availability or unavailability to handle the alarm, thereby facilitating more intelligent and rapid escalation to improve patient outcomes.

The clinician device may also include other functionality that improves other aspects of patient care. For instance, the clinician device may assist with keeping track of which patient monitoring devices are associated with which patients. Currently, clinicians type patient names into a computer system to associate patients with patient devices. Human error from mistyping may result in patients being associated with the wrong devices. Consequently, an alarm from a device may trigger a response that goes to the wrong room. As a result, a patient may not be reached in time to address the cause of the alarm or may otherwise suffer a poorer outcome.

Thus, in certain embodiments, the clinician device also includes an admit module that provides for automatic association of a patient to a device. The admit module may include a scanner application or the like that can scan a patient tag and a device tag, obtain identifiers from each tag, and couple the tags in physical computer storage (such as in an electronic medical records system). The tags may be machine-readable codes in the form of one-dimensional or two-dimensional barcodes such as UPC barcodes, quick response (QR) codes, Data Matrix codes, Aztec codes, Microsoft Tag barcodes or High Capacity Color Barcodes, Shotcode, Semacode, SPARQcode, PDF417 barcodes, Cauzin Softstrip codes, and the like, as well as radio-frequency identifiers (RFID), combinations of the same, or the like. Further, the admit component may also include functionality for associating the patient with a location such as a room, bed, bassinet (for infants), or the like.

Further, the patient monitor can include a vital signs verification component that includes functionality for initiating a vital signs submission process for an admitted patient. Once a patient has been admitted (or optionally thereafter), vital signs can be captured by the patient device and/or by the clinician and submitted via the patient device to a server system for inclusion in the patient's electronic medical record.

II. Example Clinical Computing Environment

Turning to FIG. 1, an embodiment of a clinical computing environment 100 is shown. The clinical computing environment 100 may be implemented in one or more hospitals or other clinical facilities. Further, the clinical computing environment 100 can facilitate monitoring patients within their homes if such patients are using network-enabled monitoring equipment.

In the clinical computing environment 100, various patient devices 102, clinician devices 104, and nurse's station systems or kiosks 106 communicate over a network 109 with a multi-patient monitoring system (MMS) 110. The network 109 may include a local area network (LAN), a wide area network (WAN), a public network (such as the Internet), a private network, or any combination of the same. For instance, the network 109 can include a wireless and/or wired hospital network or a network that connects multiple clinical facilities.

The patient devices 102 may be any of the patient monitors or monitoring devices described herein and may include bedside monitors, ambulatory or mobile monitors, in-home monitors, and the like. The patient devices 102 can receive input from physiological sensors coupled with a patient and may measure parameters such as oxygen saturation or $SpO_2$, respiratory rate, blood pressure, heart rate or pulse rate perfusion, other blood gas parameters, brain activity, brain oxygen saturation, any of the other parameters described herein, and the like. The patient devices 102 can provide information about a patient's status, including current values of physiological parameters, trend values, and historical values of physiological parameters over the network 109 to the MMS 110. The MMS 110 can in turn store this data in an electronic medical records (EMR) system 120.

In addition, the MMS 110 can provide this data to the nurse's station systems 106. The nurse's station systems 106 can include any type of computing device including, but not limited to, a desktop, laptop, tablet, phone or the like. The nurse's station systems 106 may also include clinical facility kiosks such as computers on wheels (COWs), which may be dispersed throughout a clinical facility. The nurse's station systems 106 can communicate with a plurality of patient devices 102 to receive information of a plurality of patients so that the nurse's station systems 106 can provide clinicians with the ability to monitor physiological parameter data for a plurality of patients.

In addition, in some embodiments (not shown) patients' rooms may be equipped with video monitoring equipment that can provide video views of patients so as to view patients remotely (e.g., for telemedicine purposes). Such video data may be provided over the network 109 to the nurse's station systems 106, to the MMS 110, and/or to clinician devices 104 (see, e.g., FIG. 17). The video data may be captured by video cameras installed in the patient devices 102 or with separate video camera installed in patient rooms or the like.

The clinician devices 104 can include any device including a laptop, tablet, cell phone, smartphone, personal digital assistant (PDA), or any other device (including desktop systems). In the depicted embodiment, the clinician devices 104 include a notification client 108 that can receive alarm notifications from the patient devices 102 through the MMS 110. In an embodiment, when a patient device 102 detects that a parameter of a patient has exceeded a threshold set in the patient device 102 (or otherwise triggered an alarm condition), the patient device 102 can send an alarm over the network 109 to the MMS 110. In turn, the MMS 110 can send the alarm or a message representing the alarm to the nurse's station systems 106 and/or the clinician devices 104.

In another embodiment, the patient devices 102 have network capability that enables the patient devices 102 to send the alarm notifications directly over the network 109 to the nurse's station systems 106 and/or to the clinician devices 104. Further, the patient devices 102 may send other types of alarms to the MMS 110, the nurse's station systems 106, and/or the clinician devices 104. Such alarms can include nonclinical alarms that may not represent that a physiological parameter has exceeded a threshold but instead may include information about a sensor that has been disconnected or otherwise has fallen off (often referred to as a probe-off condition). Likewise, a brief power outage or surge can cause the patient device 102 to reset and send a nonclinical alarm to the other devices shown. Such nonclinical alarms are sometimes referred to herein as alerts to distinguish from alarms that may be clinically actionable.

Advantageously, in certain embodiments, the notification client 108 can enable two-way communication with the patient devices 102 and the MMS 110 (and/or the nurse's station systems 106) in the event of an alarm. For instance, an alarm sent from a patient device 102 through the network 109 to the MMS 110 could be routed to the clinician device 104. The notification client 108 can receive this alarm and respond back to the MMS 110 or any other component of the computing environment 100, replying that the message was received. This provision of a reply to the alarm made by the notification client 108 can enable the MMS 110 to determine whether to escalate the alarm or not. Since the MMS 110 has received the indication that the notification client 108 received the message, the MMS 110 may determine to wait a period of time before escalating the alarm to an escalated condition (which will be described in greater detail below).

Alternatively, if the notification client 108 does not respond indicating that the client device 104 has received the alarm message, the MMS 110 may determine that some error (whether of the network 109, the clinician device 104 or otherwise) has caused the clinician device 104 to not receive the message. As a result, he MMS 110 can immediately or otherwise rapidly escalate the alarm to one or more other clinicians without having to wait a set period of time.

Thus, the two-way communication ability of the clinician device 104 can facilitate this rapid escalation because the MMS 110 can assume that if a response is not provided by the notification client 108, that the clinician device 104 likely did not receive the alarm. In an embodiment, the MMS 110 can have high confidence in this conclusion because the clinician device 104 may be locked in software or at the operating system level (e.g., in a kiosk mode or the like) so that users can access only the notification client 108 (and optionally admit module 112 or vital signs verification component 114). Accordingly, no other application access by the clinician may prevent the clinician from viewing notifications from the notification client 108, in an embodiment, resulting in a logical conclusion at the MMS 110 that if the clinician device 104 does not respond, the clinician (or device 104) did not receive the message. Thus, the clinician device 104 may be limited in software to running the notification client 108 (and optionally admit module 112 or vital signs verification component 114) and/or to some other whitelisted set of applications, such as a phone call application, a texting application, a calendaring application, or the like. Additional applications may also be whitelisted or approved to run on the clinician device 104, for example, by a provider of the notification client 108 or by the hospital organization or staff. Many other example benefits of the notification client 108 are described in much greater detail below.

For convenience, this specification primarily describes alarms as being routed through the MMS 110 to the notification client 108 and corresponding response messages being sent from the notification client 108 to the MMS 110 and optionally on to the patient devices 102. However, in other embodiments the notification client 108 can communicate directly with the patient devices 102 or nurse's station systems 106.

As described above, in the depicted embodiment, the clinician device 104 also includes an admit module 112 and a vital signs verification component 114. The admit module 112 is optional in some embodiments. Alternatively, the clinician device 104 may include the admit module 112 without including the notification client 108.

The admit module 112 may include a scanner application or the like that can scan a patient tag and a device tag, obtain identifiers from each tag, and couple the tags in physical computer storage (such as in an electronic medical records system). The tags may be machine-readable codes in the form of barcodes, quick response (QR) codes, radio-frequency identifiers (RFID), combinations of the same, or the like. Further, the admit module 112 may also include functionality for associating the patient with a location such as a room, bed, bassinet (for infants), or the like. Example embodiments of the admit module 112 are described in greater detail below with respect to FIGS. 18 and 19.

The vital signs verification component 114 can include functionality for initiating a vital signs submission process for an admitted patient. Once a patient has been admitted (or optionally thereafter), vital signs can be captured by the patient device and/or by the clinician and submitted via the patient device to a server system for inclusion in the patient's electronic medical record. The vital signs verification component 114 is described in more detail below with respect FIGS. 26 through 28.

III. Example Multi-Patient Monitoring System Features

Figure 2:
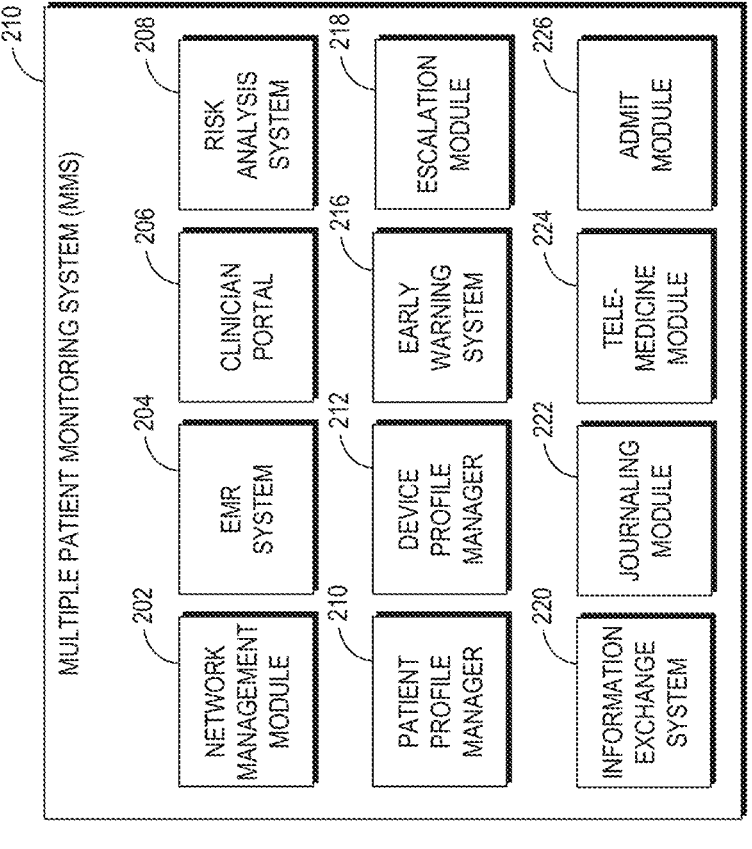
FIG. 2 depicts a more detailed embodiment of the multi-patient monitoring system of FIG. 1.

Turning to FIG. 2, a more detailed embodiment of a multi-patient monitoring system (MMS) 110 is shown, namely, an MMS 210. The MMS 210 can have all of the features of the MMS 110 described above. In the depicted embodiment, the MNS has several subsystems or modules that can be implemented in hardware and/or software. The example modules or components shown group functionality of embodiments of the MMS 210 together under logical descriptions. It should be understood, however, that the various modules and systems shown in the MMS 210 or portions thereof could be implemented together in a single system. In addition, not all of the systems or modules shown need be implemented on the same computing device but could instead be implemented in separate computing devices. Further, some of the modules shown may be omitted in various embodiments.

Certain aspects of the MMS 210 are described as being implemented across multiple clinical facilities. However, the MMS 210 may be implemented in a single clinical facility in other embodiments, and thus, some of the features described herein may be less applicable or not applicable at all to a single-facility installation of the MMS 210. More detailed example features of the MMS 210, any of which may be combined with the features described herein, are disclosed in U.S. application Ser. No. 14/030,360, filed Sep. 18, 2013, titled "Intelligent Medical Network Edge Router" ("the '360 application"), the disclosure of which is hereby incorporated by reference in its entirety and which is included as an Appendix hereto.

The MMS 210 includes, for example, a network management module 202. The network management module 202 can manage network communications with other networks, including networks in hospitals and other facilities as well as communications with mobile patient devices and clinician devices. For example, the network management module 202 can communicate with devices in hospitals and outside of hospitals, or inside of facilities and outside of facilities. The network management module 202 can provide networking services such as load balancing, failover, and the like. In addition, if a patient is monitored in a facility that communicates with the network management module 202, and then the patient is discharged from the facility, the network management module 202 can maintain connectivity with a body-worn or other mobile medical device associated with the patient, for example, over cellular or Wi-Fi links.

The MMS 210 also includes an EMR system 204 that can generally store patient data from any facility, including data collected from patient monitoring devices in patients' homes or while patients are mobile outside of their homes or out of facilities. For example, the EMR system 204 can include such information as parameter values, trend values, alarm histories, patient demographic data, patient condition data including diagnoses, patient medical histories, and patient medications, among a variety of other patient data. The data in the EMR 204 can advantageously be used by other components of the MMS 210 as described below to improve patient care. The EMR system 204 can also store data received from the vital signs verification component 114 described above and in more detail below with respect FIGS. 26 through 28.

A clinician portal 206 of the MMS 210 can provide a user interface or user interfaces that can be accessed by clinicians via their clinician devices to monitor the health status of their patients for whom they are responsible. The clinician portal 206 may, for example, be implemented in one or more web pages, mobile applications, or other network applications and may provide information about the wellness or relative wellness of each patient.

In one embodiment, a wellness score or index is computed for some or all patients by a risk analysis system 208 of the MMS 210, and the clinician portal 206 can depict these wellness indices among other parameter data, trend data and alarms for each patient. In one embodiment, the clinician portal 206 facilities triaging patients by providing functionality for patients to be ordered or ranked based on their wellness scores or indices as computed by the risk analysis system 208. Example features for computing wellness indices or risk assessments and which may be implemented herein are described in U.S. application Ser. No. 13/269,296, filed Oct. 7, 2011, titled "Risk Analysis System," and Ser. No. 13/371,767, filed Feb. 13, 2012, titled "Medical Characterization System," the disclosure of which is hereby incorporated by reference in its entirety. For example, the risk analysis system 208 can take into two or more parameters, such as any combination of the following parameters: oxygen saturation (e.g., $SpO_2$), respiratory rate, pulse rate, heart rate, total hemoglobin level, methemoglobin, carboxyemoglobin, blood pressure, ECG output, encephalography output, or the like. The risk analysis system 208 can combine data from such parameters and reduce this data to a single value or data representation of the combination of those parameters. The single value may be, for example, an index or score that is on a scale of 0 to 10, where 10 may represent a most healthy state, while 0 may represent a least healthy state. Thus, such scores could be used to rank the relative health state or acuity of patient sicknesses and such numerical rankings can be output for presentation to clinicians in the clinician portal 206, thereby enabling clinicians to quickly triage patients.

In some embodiments where the MMS 210 is implemented for multiple clinical facilities, the risk analysis system 208 also leverages aspects of the cloud-based infrastructure of the MMS 210 to improve the wellness index calculation. For example, the risk analysis system 208 may be able to access patient profile data from the MMS 210 that comes from previous hospital visits or other clinical facility visits from a single facility or multiple facilities to compute historical wellness indices or to compute a current wellness index. The risk analysis system 208 can also personalize the wellness index based on patient attributes stored in the EMR system 204. For example, the risk analysis system 208 can personalize which parameters are weighted more heavily in the combination of parameters that are output as a wellness index based on previous patient conditions listed in EMR system 204. In currently available systems, different institutions typically do not share their EMR data, and EMRs therefore cannot be used to correlate patient data from multiple institutions together and thereby improve risk analysis and wellness indices. However, such advantages can be made possible in certain embodiments by the centralized cloud nature of the MMS 210.

The MMS 210 also includes a patient profile manager 211. The patient profile manager 211 can manage patient profiles, which can include information about patient demographics, patient alarm settings, including alarm settings from previous visits to potentially multiple different facilities, patient conditions and so forth, and example features of which are described in greater detail below with respect to FIG. 3. The MMS 210 further includes a device profile manager 212 that can manage and store device profiles for medical devices that interact with the MMS 210 as well as optionally other computing devices. The profiles may have information about rules that can be used to track the usage of these devices as well as a variety of other features.

The MMS 210 also includes an early warning system 216. The early warning system 216 can issue early warning alarms based on parameter measurements, indices such as the wellness index or other indices. The early warning system 216 can look for patterns in patients to facilitate detecting never events, including events that should occur never or rarely, like a patient dying in bed without any intervention, particularly when a patient is home and would not ordinarily be under the care of a hospital or have access to a system like the risk analysis system 208 or the early warning system 216.

An information exchange system 220 of the MMS 210 can facilitate communicating information about patients to government or research institutions 118 described above with respect to FIG. 1. One scenario where patient information may be submitted (anonymously) to government or research institutions is where a disease outbreak has occurred. For example, information may be provided that indicates several patients in a hospital have come down with the flu. The information exchange system 220 can report this occurrence to an external entity such as the CDC or the Center for Disease Control, or state or local government agency or national government agency or worldwide agency to alert such agencies other institutions of the potentiality of a disease outbreak. If multiple institutions are using the services of the MMS 210, then such information about patient conditions can be correlated and provided to these institutions as described above. More generally, the information exchange system 220 can provide data about changing patient conditions continuously or periodically to government or research organizations to enable such organizations to rapidly respond to changes in regional health issues.

Further, the data provided by the information exchange system 220 can be valuable to government agencies or research institutions to determine the effects of local conditions on health conditions. It may be discovered, for instance, that patients that go to a specific facility or set of facilities in a region are afflicted with disease related to nearby coal mining which can be ascertained by research institution or a government agency that has responsibility over such activities. Accordingly, the information exchange system 220 can provide value data that can provide reports that can be used by external entities to improve patient care.

A journaling module 222 of the MMS 210 can capture clinician interactions with medical devices that are in the institutions and/or that are in patients' homes or that are body worn in mobile situations. The interactions can include any type of button press, alarm setting change, machine-readable code (e.g., 1-D or 2-D barcode) or RFID tag interaction, or the like and can be recorded for the purposes of determining clinician response times to alarms or other measures of the quality of a clinician's care. The journaling module 222 can further leverage the centralized monitoring capabilities of the MMS 210 to compare the quality of care as journaled or otherwise calculated amongst different institutions as an apples-to-apples comparison because some or all of the data from these institutions can be provided to the centralized MMS 210.

Further, the journal module 222 can facilitate comparing the quality of care between different units in a hospital or other facility including different floors or groups of clinicians or shifts, or the like. The journal module 222 can also facilitate comparing similar groups amongst different facilities, such as an ICU group in two different facilities, and can thereby enable an organization to identify gaps or deficiencies of care in different facilities that can be corrected. This information can be provided in real time or near-real time so that adverse patient care outcomes can be quickly addressed, in contrast to the past where information about quality of care is often analyzed well after an adverse care event has occurred (or even after a patient has been discharged). Further embodiments of journaling and detecting clinician interactions with devices (including via RFID tags) are described in U.S. application Ser. No. 14/032,132, filed Sep. 19, 2013, titled "Medical Monitoring System" ("the '132 application"), the disclosure of which is hereby incorporated by reference in its entirety.

A telemedicine module 224 of the MMS 210 can facilitate telecommunications between clinicians and patients, including telepresence communications where clinicians can diagnosis, treat, or otherwise attend to the needs of patients remotely using audio visual systems or the like. In some embodiments, the telemedicine module 224 can also be used in conjunction with features of the escalation module 218 described below.

The escalation module 218 can provide functionality for escalating alarms from a first or primary care provider to a second or subsequent care provider in case the primary care provider is unavailable. In certain embodiments, the escalation module 218 can perform escalation as follows (or the like). If an alarm is received from a patient device, the escalation module 218 can initially supply an alarm notification message regarding the alarm to one or more clinician devices 104. These clinician device(s) 104 may correspond to a primary care clinician or group of clinicians who have primary responsibility for the patient for whom the alarm was made. (Any of the alarms described herein, including escalation alarms and reescalation alarms, may be provided to a group of clinicians rather than to a single clinician. However, for ease of explanation, many examples herein use a single clinician in the alarm message.) If no response to this initial alarm message is provided by the clinician device 104 (or the notification client 108 installed thereon), the escalation module 218 can escalate to a second clinician or group of clinicians by sending the alarm notification message to the second clinician or second group of clinicians. This escalation may optionally include sending the alarm notification message to the primary clinician or group of clinicians as well. The alarm notification message may indicate that it is an escalated message to reflect an increased urgency of the alarm.

If no response is provided by the clinician device(s) 104 to the escalation module 218 or, alternatively, if the alarm continues to be provided by the patient device 102 to the escalation module 218, the escalation module 218 can re-escalate. In an embodiment, the escalation module 218 re-escalates by sending the alarm notification message or a similar alarm message to a supervisor such as a charge nurse or an administrator who has responsibility over a group of patients. In addition, this reescalation message may be sent to the first and/or second groups of clinicians as well. The alarm notification message may indicate that it is a re-escalated message to reflect an even greater urgency of the alarm. As used herein, in addition to having its ordinary meaning, "escalation" can include re-escalation. Thus, for example, an alarm may initially be sent, escalated, and escalated again (e.g., re-escalated).

In an embodiment, since the notification client 108 described above can respond to the escalation module 218, the escalation module 218 can manage escalations more intelligently. For instance, the escalation module 218 can detect whether the clinician device has received an alarm notification message, an escalation message, or a re-escalation message. If the message has not been received, the escalation module 218 can escalate or re-escalate the alarm. In addition, if a clinician indicates through the notification client 108 that he or she cannot address the alarm, the escalation module 218 can automatically escalate or re-escalate the alarm. Additional embodiments of interactions between the escalation module 218 and the notification client 108 are described in greater detail below with respect to FIGS. 3 and 4.

As described above, the escalation module 218 can send an initial alarm to a first clinician or group of clinicians, escalate the alarm to a second clinician or group of clinicians, and re-escalate the alarm to a third clinician or group of clinicians. While these groups may be defined before the alarm occurs, in some embodiments, the escalation module 218 uses location-based rules to dynamically select which clinicians to send an alarm to (whether initially or via escalation/re-escalation). The location-based rules can take into account which clinicians are closer to the patient. For instance, the escalation module 218 can initially send an alarm to a clinician closest to a patient, then escalate to clinicians in closer proximity to the patient than other clinicians, and so on.

The escalation module 218 may know the locations or approximate locations of the clinicians because the clinician devices 104 may include location-tracking hardware and/or software that can report their locations to the escalation module 218. The location-tracking hardware and/or software can use triangulation techniques to determine clinician location, for example, by triangulating with wireless access points within a clinical facility (or cell towers to triangulate inside or outside a facility). The location tracking hardware and/or software may instead use global positioning system (GPS) features to track clinician location. Other location-tracking techniques can include dead-reckoning or dead-reckoning combined with any of the above techniques for calibration. In addition, in some embodiments, the escalation module 218 can implement any of the location-based escalation rules or clinician location tracking techniques described in the '132 application, incorporated above.

In other embodiments, the escalation module 218 may send alarms to or escalate to clinicians who are not close by the patient and who may, in fact, be geographically remote from the patient. Send alarms or escalations to such clinicians may be possible because such clinicians can use telepresence or telemedicine techniques to interact with patients. The telemedicine module 224 may provide remote clinicians with access to patient parameter data, trend data, and/or video data, enabling remote clinicians to intervene in at least some alarm situations. In some situations, a remote clinician can instruct a local clinician on techniques to be used to remediate an alarm and care for a patient. For instance, a doctor or specialist may remotely instruct a nurse on how to care for a patient undergoing an alarm condition. The escalation module 218 may use other remote escalation techniques described in the '360 application, incorporated above.

The MMS 210 also includes an admit module 226 in the depicted embodiment. The admit module 226 may communicate with the admit module 112 installed in the clinician device(s) 104. As described above, the admit module 112 in the clinician device(s) 104 may include a scanner application or the like that can scan a patient tag and a device or location tag, obtain identifiers from each tag, and couple the tags in physical computer storage (such as in an electronic medical records system). This coupling can include sending a message from the admit module 112 to the admit module 226. The admit module 226 can receive the patient identifier and device or location identifier(s) from the admit module 112 and associate the identifiers in physical computer storage, such as in the EMR system or another database. For instance, the admit module 226 can create a data record in a database that includes both the patient identifier and a device and/or location identifier. Further, the admit module 226 can receive a clinician identifier from the admit module 112 and store the clinician identifier together with the patient identifier and/or device/location identifier(s). This information may be accessed by the escalation module 218, among other modules, to properly identify which devices, locations, and/or clinicians are associated with a patient so to send alarm notification messages with proper identifying information to the proper clinicians.

IV. Example Alarm Notification Processes

Figure 3:
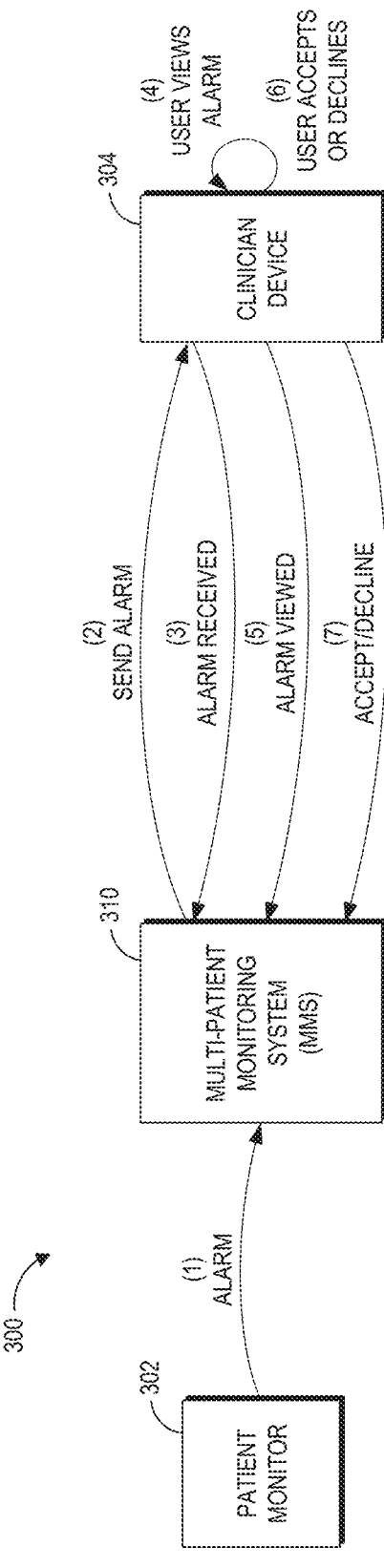
FIG. 3 depicts an example alarm lifecycle flow diagram.

Turning to FIG. 3, an example alarm lifecycle flow 300 is shown. The flow 300 depicts an example state flow of an alarm notification message from a patient monitor 302 to receipt by a clinician device 304. In an embodiment, the lifecycle flow 300 depicts examples of how the clinician device 304 can respond to the alarm so as to improve patient outcomes. The patient monitor 302 is an example embodiment of the patient monitor 102. Likewise, the clinician device 304 is an example embodiment of the clinician device 104. Also shown is a multi-patient monitoring system (MMS) 310, which may have some or all the functionality of the MMS 110 or 210.

In the depicted embodiment, the patient monitor 302 at state 1 issues an alarm to the MMS 310. The alarm may be a clinical alarm or a nonclinical alarm as described above. At state 2, the MMS 310 sends an alarm notification message to the clinician device 304. A notification client (not shown; see FIG. 1) in the clinician device 304 can indicate that the alarm was received at state 3 by providing a return message to the MMS 310. As a result, the MMS 310 can know that the alarm was received by the clinician device 304 and therefore justifiably wait a period of time to escalate. In contrast, if the alarm had not been indicated as being received by the clinician device 304 to the MMS 310, the MMS 310 may rapidly escalate (see, e.g., FIG. 4).

At state 4, a user of the clinician device 304 may view the alarm using, for example, the notification client 108. The user may view the alarm in a variety of ways. Generally speaking, the notification client 108 can depict a user interface that shows some aspect of the alarm on a lock screen of the notification client 108, on an active alerts screen, or on an application screen of the notification client 108. The notification client 108 may consider the alarm as being viewed if the clinician device 304 changes state from locked to unlocked (e.g., via button press by the clinician) and if the lock screen depicts the alarm (see, e.g., FIG. 5 below). In another embodiment, the notification client 108 considers the alarm as being viewed if the clinician unlocks the lock screen and views a list of alarms including this particular alarm (see, e.g., FIG. 6). In another embodiment, the notification client 108 considers the alarm as being viewed if the clinician unlocks the lock screen, views a list of alarms including this particular alarm, and then selects this particular alarm (see, e.g., FIG. 7).

At state 5, the clinician device 304 reports to the MMS 310 that the alarm has been viewed. This state may also be implemented by the notification client 108 by reporting that the alarm has been viewed. The notification client 108 of the clinician device 304 can enable the MMS 310 to know that the clinician is now aware of the alarm and not just that the clinician's device 304 has received the alarm. Knowing (or, equivalently, receiving or storing an indication in the MMS 310) that the clinician has viewed the alarm can further increase confidence that the clinician may respond to the alarm. Conversely, if the alarm had been received by the clinician device 304 but had not been indicated as being viewed by the clinician, the MMS 310 might hasten escalation to another clinician or set of clinicians (see, e.g., FIG. 4).

At state 6, the user can accept or decline to handle the alarm, for example, by inputting an indication of acceptance or declining to the clinician device 304. The notification client 108 may, in some embodiments, infer the clinician's decision to accept handling or decline handling the alarm based on the user's input. For instance, if the clinician marks an alarm notification message as "unread" (e.g., similar to marking an email as unread), then the notification device client 108 may infer that the clinician has decided not to handle the alarm. At state 7, the clinician device 304 reports to the MMS 310 whether the clinician has decided to accept or decline the alarm. If the clinician has declined to handle the alarm, the MMS 310 can rapidly or immediately escalate the alarm to another clinician or set of clinicians.

In one embodiment, acceptance is not provided as an option in the notification client 108 because a clinician may directly respond to the alarm without indicating his acceptance of the alarm. Likewise, many other aspects described herein are optional and may be omitted or added thereto in other embodiments.

Figure 4:
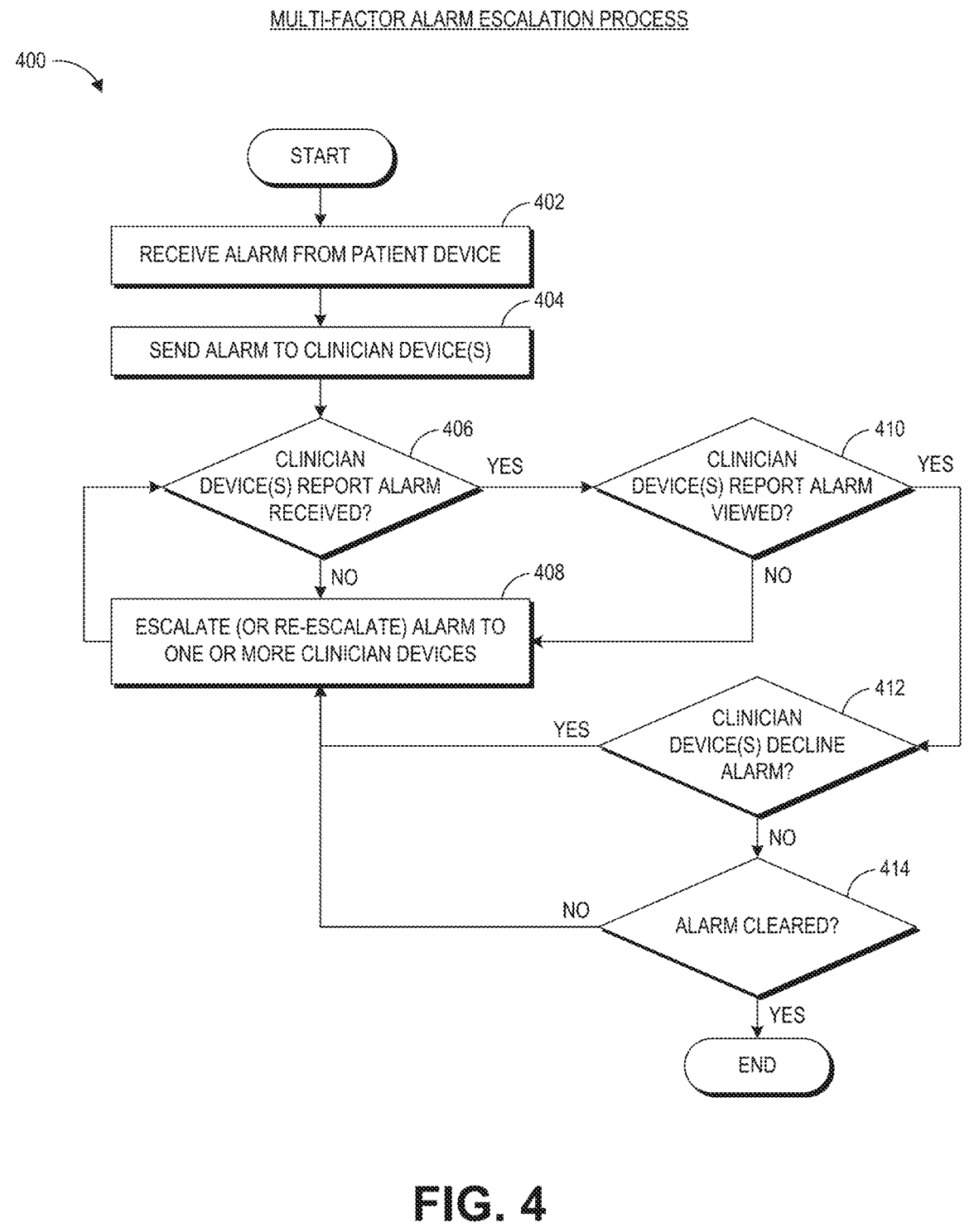

Turning to FIG. 4, an embodiment of a multi-factor or two-way alarm escalation process 400 is shown. The alarm escalation process 400 may be implemented by any of the systems described herein including the MMS 110, MMS 210, or MMS 310. For convenience, the alarm escalation process 400 will be described in the context of the escalation module 218 of the MMS 210, although other computing systems not described herein may implement the alarm escalation process 400. In certain embodiments, the alarm escalation process 400 can advantageously provide improved patient outcomes by more rapidly responding to alarms via escalation due to the two-way nature of the alarm message lifecycle described herein.

At block 402, the escalation module 218 receives an alarm from a patient device and sends the alarm to a clinician device or devices at block 404. At decision block 406, it is determined by the escalation module 218 whether the clinician device or devices report the alarm having been received. If not, at block 408, the escalation module 218 escalates the alarm to one or more other clinician devices, which may but need not include the initial clinician device or devices to which the initial message was sent.

In an embodiment, if the initial message was sent to a single clinician device and at block 406 it is determined that the clinician device did not report receiving the message, escalation happens automatically at block 408. In another embodiment, when the initial message is sent to a plurality of clinician devices, block 406 does not trigger escalation at block 408 until it is determined that none of the clinician devices reported receiving the alarm. Alternatively, the escalation module 218 can implement a hybrid approach where if any of a plurality of client devices have not responded as receiving the message, the escalation module 218 can escalate at block 408. In another embodiment, the escalation module 218 escalates if a majority of the client devices did not receive the alarm or indicate having received the alarm message. Other embodiments are possible.

If, at decision block 406, the clinician device or devices reported receiving the alarm, then it is further determined by the escalation module 218 at block 410 whether the clinician device or devices reported the alarm being viewed by a user. If not, then the escalation module 218 can escalate or re-escalate the alarm at block 408 to one or more clinician devices. As used herein, in addition to having its ordinary meaning, the term "re-escalate" can refer to escalating a second time or any successive time after a previous escalation has occurred.

As with the decision block 406, the decision block 410 can select a different output depending on the number of clinician devices to which the alarm was sent. If a plurality of clinician devices received the alarm, then the escalation module 218 may proceed to block 408 and escalate if just one of them did not indicate that the user viewed the message. In another embodiment, escalation occurs at block 408 if a majority did not view the message, or if all did not view the message, or the like.

If the clinician device or devices reported the alarm being viewed at block 410, the process 400 proceeds to block 412. At block 412, the escalation module determines whether the clinician device or devices declined the alarm. If the clinician device or devices declined the alarm, then the escalation module 218 proceeds to escalate or re-escalate at block 408. As with the previous decision block 406 and 410, the escalation may occur at block 408 via block 412 if a single device declined the alarm or if a majority or all of the devices declined the alarm, depending on the implementation. If one or more devices did not decline the alarm at block 412, then the escalation module 218 awaits to determine whether the alarm has been cleared at block 414. If the alarm has been cleared, the process 400 ends; otherwise, the escalation module 218 escalates or re-escalates at block 408.

In certain embodiments, if multiple parameters are alarming at the same time or together (e.g., one after another and the first has not yet been cleared by clinician or on its own), the process 400 may be modified. For instance, any step in the process may be truncated in time, e.g., by shortening wait times, to escalate faster at any point in the process 400.

V. Example Alarm Notification User Interfaces

FIGS. 5 through 17 depict several example user interfaces that may be implemented in a clinician device 504. The user interfaces shown depict example output of the notification client 108 described above and may be implemented in any of the clinician devices described herein. The example clinician device 504 shown in FIGS. 5 through 17 may have any of the features of the clinician devices described above.

The user interfaces shown may be implemented in a mobile application such as an application that runs on a mobile operating system such as the Android™ operating system available from Google™ or the iOS™ operating system available from Apple™. Alternatively, or in addition to being a mobile application, the user interfaces shown can be implemented in a web application that runs in a browser. Thus, the notification client 108 may be a mobile application or may be a browser, or in some embodiments, may include the functionality of both.

The user interfaces shown are merely examples that illustrate some example embodiments described herein and may be varied in other embodiments. For instance, user interface controls shown may include buttons, touch-selective components and the like which may be altered to include any type of user interface control including, but not limited to, checkboxes, radio buttons, select boxes, drop-down boxes, textboxes or any combination of the same. Likewise, the different user interface controls may be combined or their functionality may be spread apart amongst additional controls while retaining the similar or same functionality as shown and described herein with respect to FIGS. 5 through 17. Although touchscreen interfaces are shown, other clinician devices may implement similar user interfaces with other types of user input devices such as a mouse, keyboard, stylus, or the like.

Figure 5:
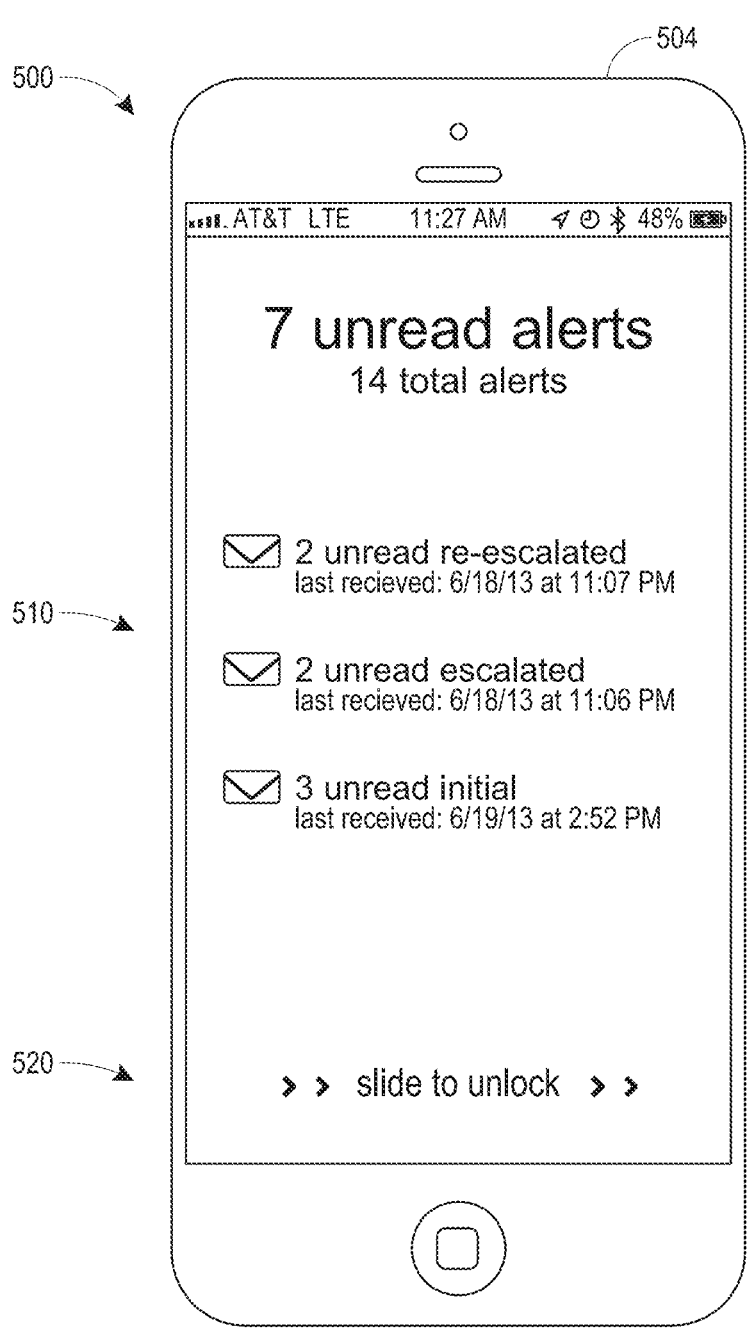
FIGS. 5 through 17 depict example clinician device user interfaces.

Turning specifically to FIG. 5, the clinician device 504 is shown depicting a lock screen user interface 500. The lock screen user interface 500 may be shown when the clinician device 504 comes out of a sleep mode or is otherwise unlocked by a user. The lock screen user interface 500 may be displayed, for instance, if the user presses a power button on the device 504 or if the device 504 receives an alarm notification.

The example lock screen user interface 500 shows lock screen notifications 510 which, in the depicted example, list three unread initial alarms, two unread escalated alarms, and two unread re-escalated alarms. In an embodiment, these alarms can be output by the notification client 108 to the lock screen. A user may select an unlock mechanism 520 on the lock screen user interface 500 to unlock the clinician device 504 and be presented with other user interfaces such as a user interface 600 shown in FIG. 6.

Figure 6:
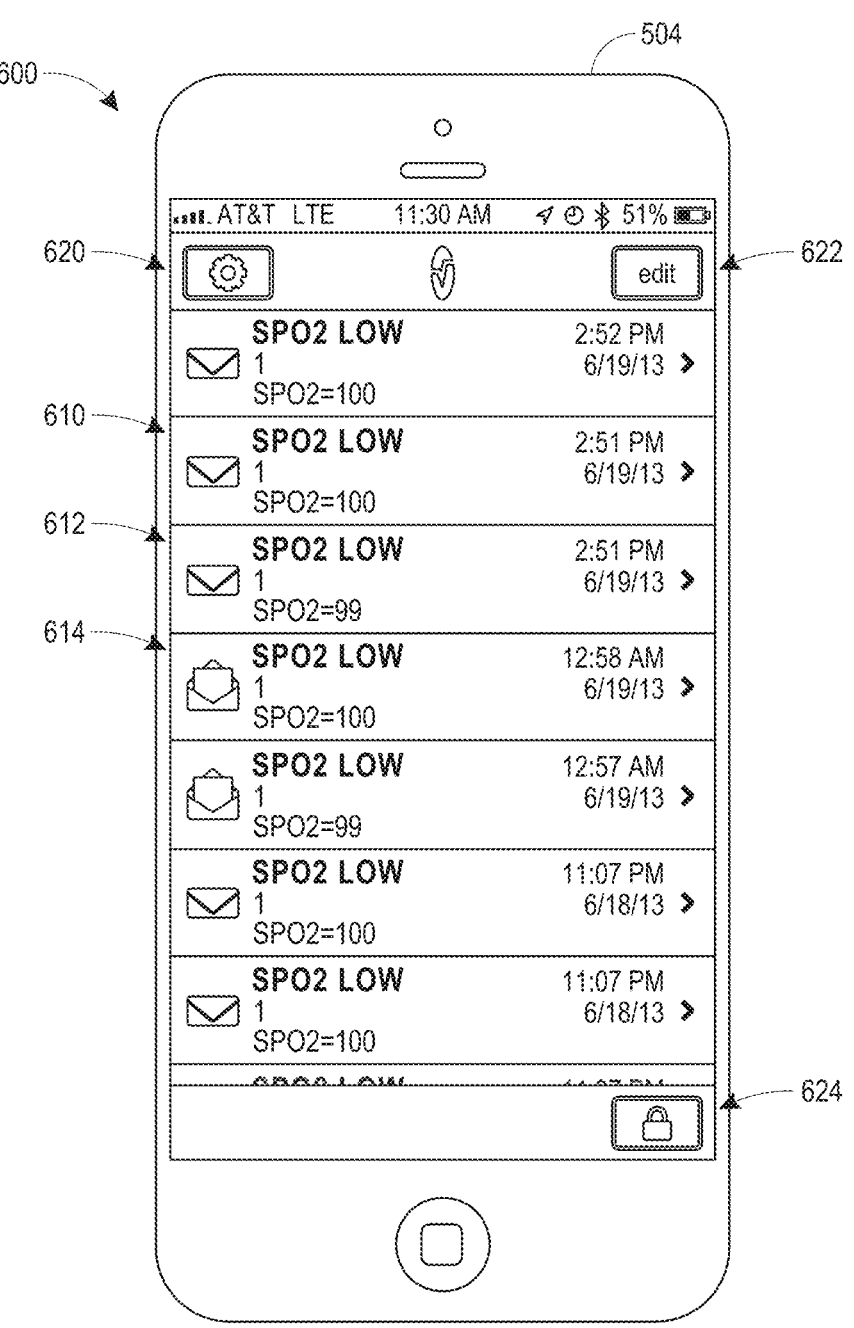

With reference to FIG. 6, the user interface 600 depicts a list of example alarm notifications 610 in more detail. Each notification 610 includes, in the depicted embodiment, information about the type of the alarm, whether it is an initial alarm, escalation, or reescalation; information about the patient, including the patient's identifier such as a room number of the patient; the time and date of the alarm; the parameter value associated with the alarm; and the like. An alarm type icon 612 shown next to each notification 610 can indicate the type of alarm whether it be an initial alarm, an escalation alarm, or a re-escalated alarm. The alarm type icon 612 is an envelope in the depicted embodiment and may be a different color depending on the type of the alarm. For instance, the alarm type icon 612 can be blue for an initial alarm, yellow for an escalated alarm, and red for a re-escalated alarm to indicate the degree of severity of those alarms, although other colors may be chosen. Another icon 614 depicts an open envelope, indicating that the notification has already been viewed by the user.

Other user interface elements may be chosen to indicate whether the alarm is an initial, escalation, or reescalation alarm. For example, the type of alarm may be spelled out with text in the user interface 600 as an initial, escalation, or reescalation alarm. The alarm might be indicated as the "1st" alarm, "2nd" alarm, or "3rd" alarm with numbers or the like, or with letters such as A, B, C, and the like. Further, an abbreviation such as "I" for initial, "E" for escalation, and "R" for reescalation may also be displayed. Although three different types of alarms are described herein, it should be understood that one or more additional levels of escalation may be displayed. Alternatively, there may be fewer than three levels of alarms, such as just an initial alarm and an escalated alarm.

Other options shown include a settings control 620 that enables a user to affect settings of the notification client. Selection of the settings control 620 can cause the user interface shown in FIG. 15 to be displayed, which is described in detail below. In addition, an edit control 622 is shown that enables deleting old notification 610. Selection of the edit control 622 can cause user interfaces such as are described below with respect to FIGS. 13 and 14 to be displayed. A lock control 624 is also shown that enables the user to put the client device 504 in a lock state, outputting a user interface such as the lock screen user interface 500 of FIG. 5.

Figure 7:
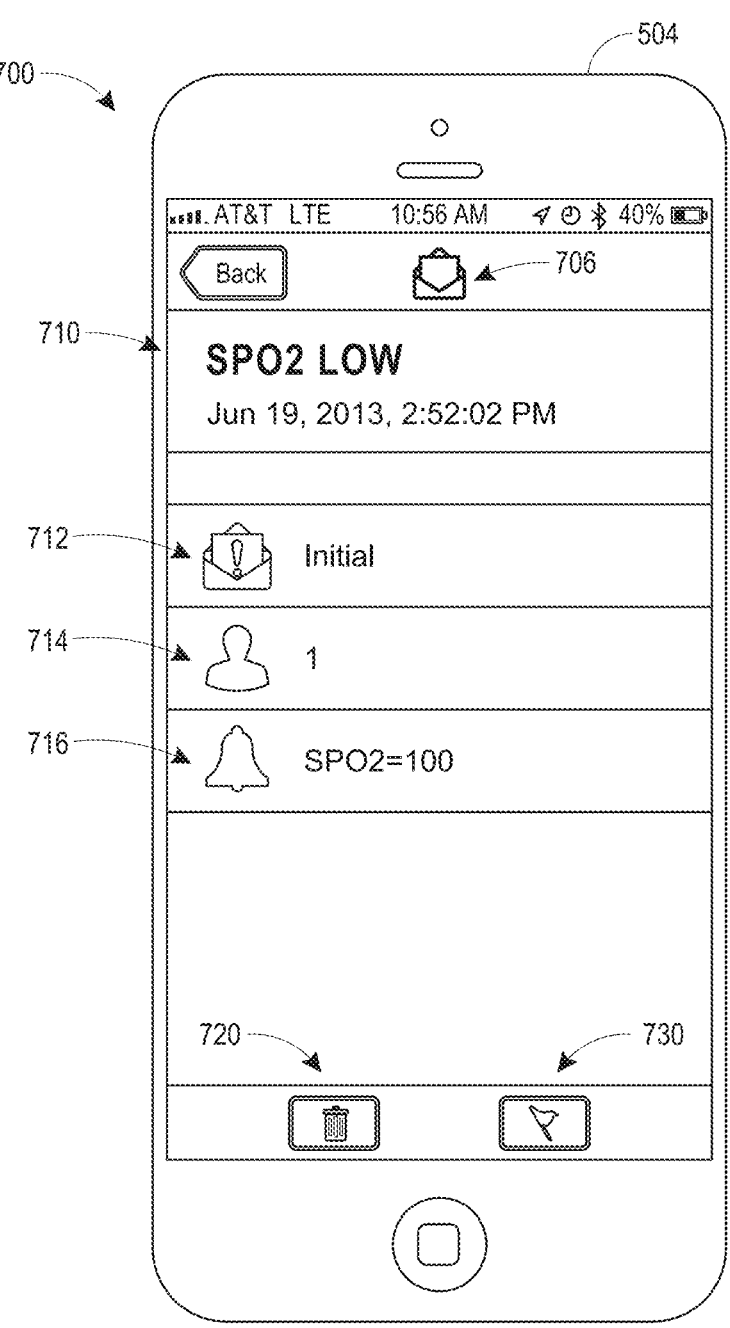
Figure 8:
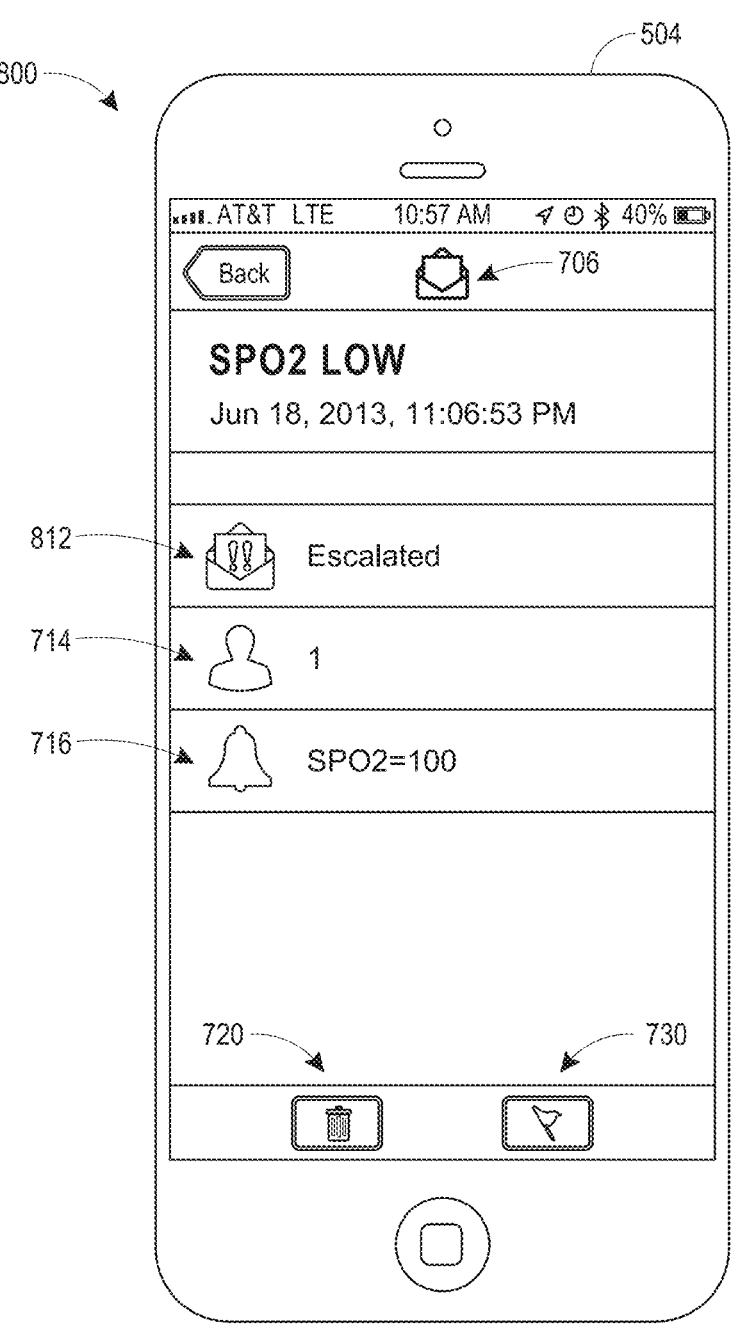
Figure 9:
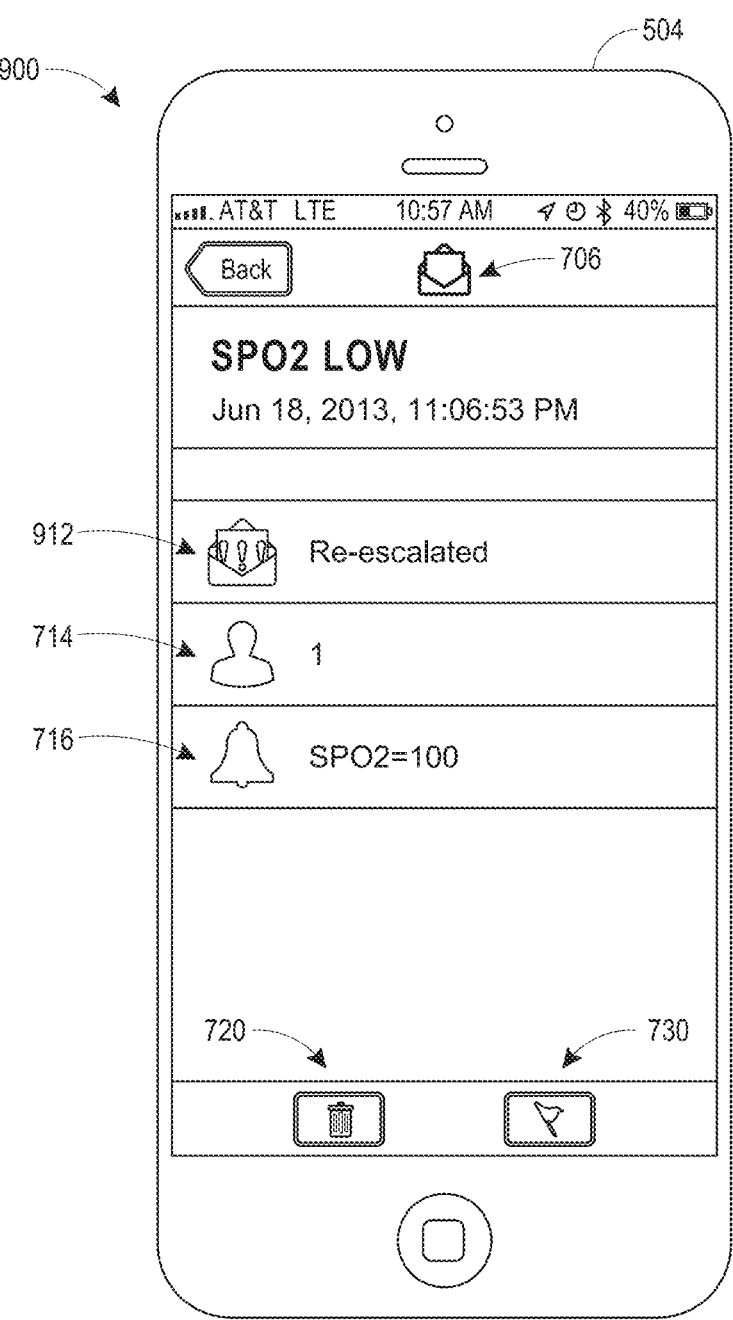

Selection of any of the notifications 610 can cause user interfaces such as the user interfaces 700, 800 or 900 of FIG. 7, 8, or 9, respectively, to be displayed. FIG. 7 in particular depicts a user interface 700 for an initial alarm notification, FIG. 8 depicts a user interface 800 of an escalated alarm notification, and FIG. 9 depicts a user interface 900 of a re-escalated alarm notification.

With specific reference to FIG. 7, the user interface 700 includes information about the notification 710, a message read icon 706 indicating that the message has been opened, a notification type icon 712 that indicates that this is an initial alarm, and a room number 714 and a parameter value 716, which in this is depicted by $SpO_2$. In an embodiment, the user can select the parameter value to see additional details about the user including a trend of the parameter value 716 over time, other historical data, or the like. In addition, other user interface controls may be provided in the user interface 700 (or 800 or 900) to access this trend and more detailed parameter information. Further, a user interface control may be provided for accessing a video of the user as described in greater detail below. Other controls, including a control 720 for deleting the message and a control 730 for marking the message unread are also shown. Selecting the control 730 can cause the user interface shown in FIG. 10 to be displayed, which will be described in greater detail below.

Turning to FIG. 8, many of the same features described with respect to FIG. 7 are shown with the difference that the notification type icon 812 is an escalated type icon. Likewise in FIG. 9, similar features are shown as in FIGS. 7 and 8 except that a notification type icon 912 indicates that this is a re-escalated alarm.

Figure 10:
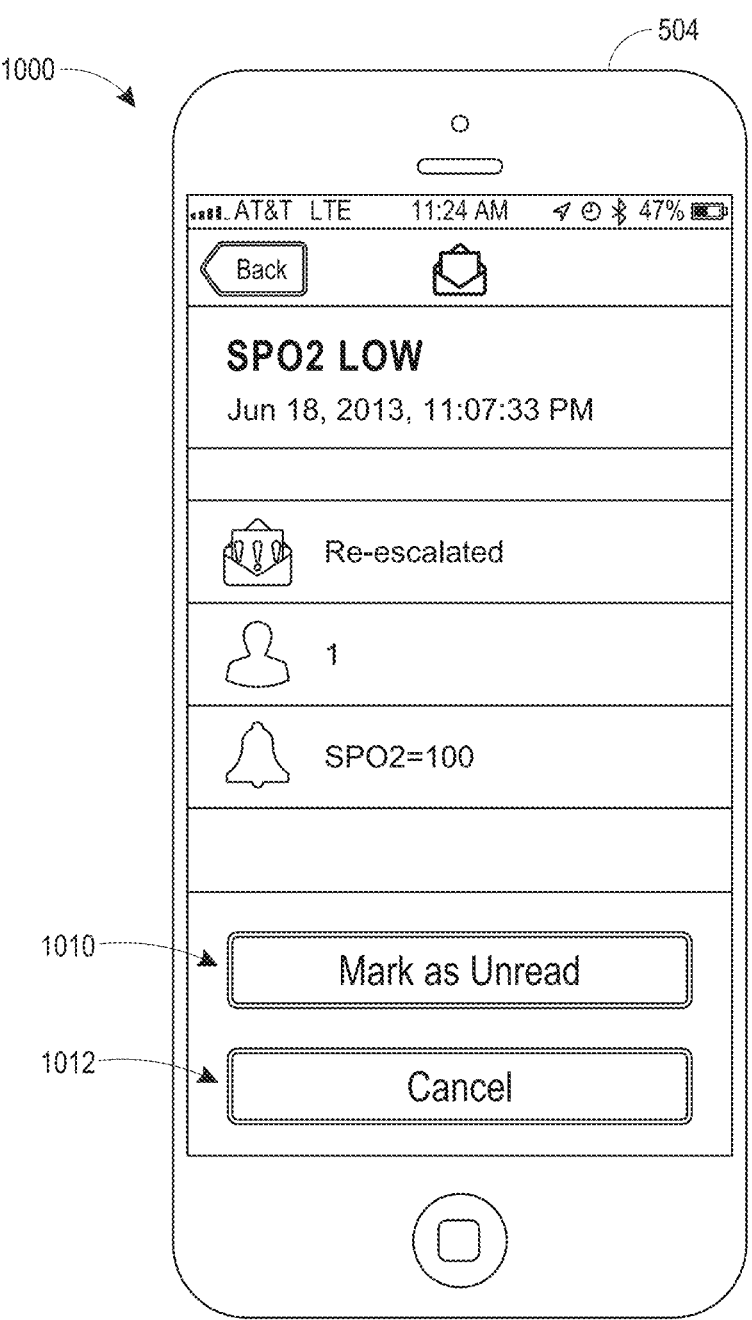
Figure 11:
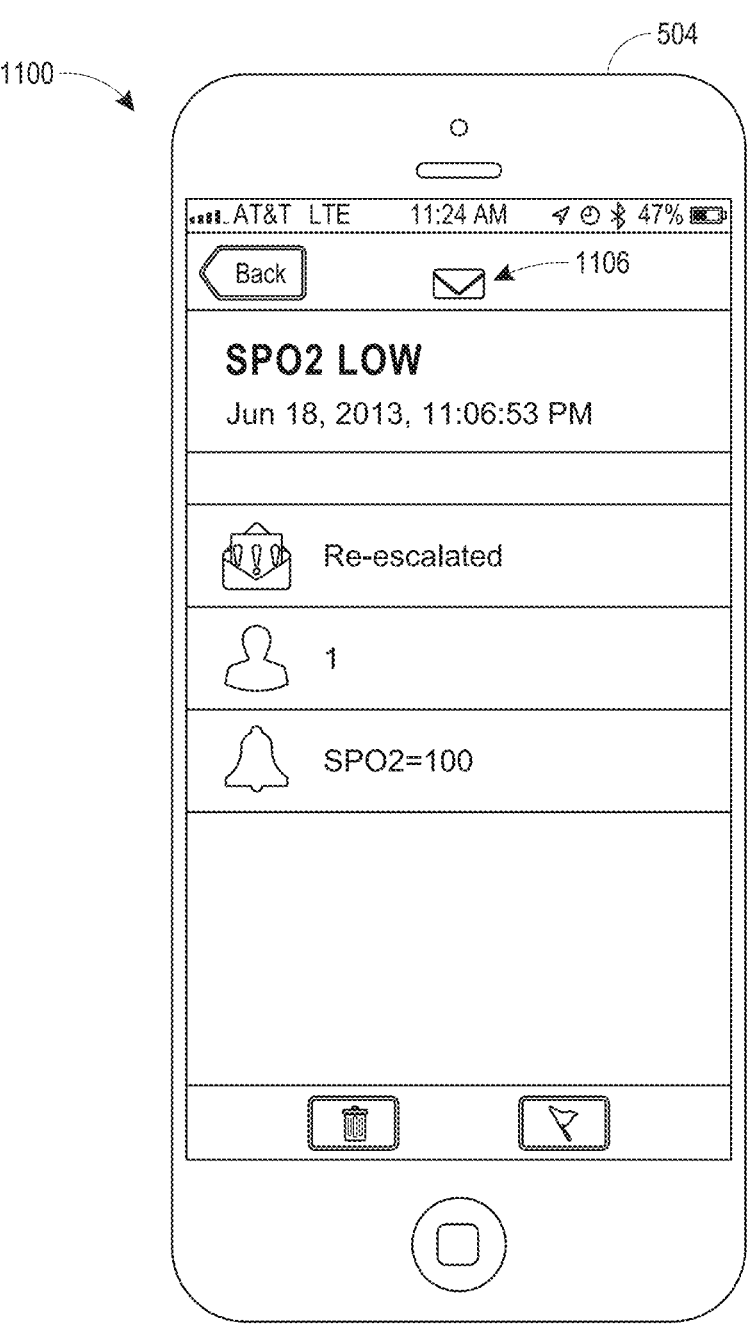

Turning to FIG. 10, selection of the mark unread control 730 from FIG. 7, 8 or 9 can cause the user interface 1000 to be shown. The user interface 1000 includes a button 1010 to confirm that the message is to be marked unread as well as a button 1012 to cancel the marking of the message being unread. If the message is marked unread, then the notification client 108 can send a message to the MMS that indicates that the clinician has declined to handle this alarm. The MMS can then use this message to automatically escalate rapidly unless perhaps other members of the team have not yet marked their messages unread (see FIG. 4). Marking the message as unread can cause a user interface 1100 shown in FIG. 11 to be shown which is similar to the user interfaces 700, 800 and 900 except that the user interface 1100 includes a message unread icon 1106 at the top of the user interface 1100.

Figure 12:
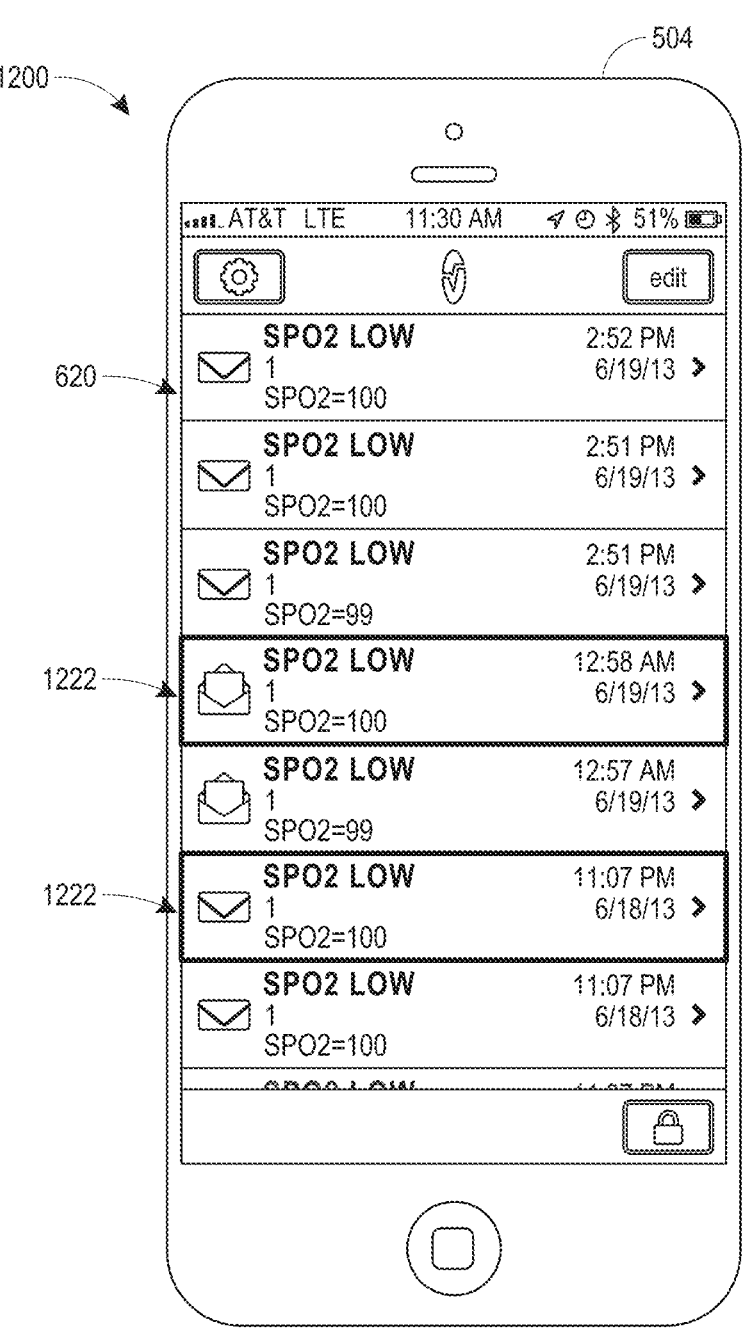

FIG. 12 shows a user interface 1200 that is another view of the user interface 600 of FIG. 6, including the notifications 620 described above as well as alarm cleared indicators 1222. The alarm cleared indicators 1222 are, in the depicted embodiment, boxes that surround a few of the notifications 620 shown. The boxes may be green or some other color that indicates that the alarm has been cleared. Other ways to show that the alarm has been cleared may include making the background color of the notification 620 green or some other color, or graying out the notification 620 for which their alarms are cleared, or collapsing them so that they are no longer visible on the display, or archiving them, for example, by auto-deleting them. However, in an embodiment, auto-deleting notifications when an alarm is cleared can be confusing for a clinician especially since some patients go in and out of alarm states rapidly, which could potentially cause flickering of alarms. Auto-deletion of alarm notifications upon alarm clearance could also cause confusion for clinicians. Thus, alarms are not auto deleted in some embodiments but instead are otherwise marked with their status as being cleared.

Figure 13:
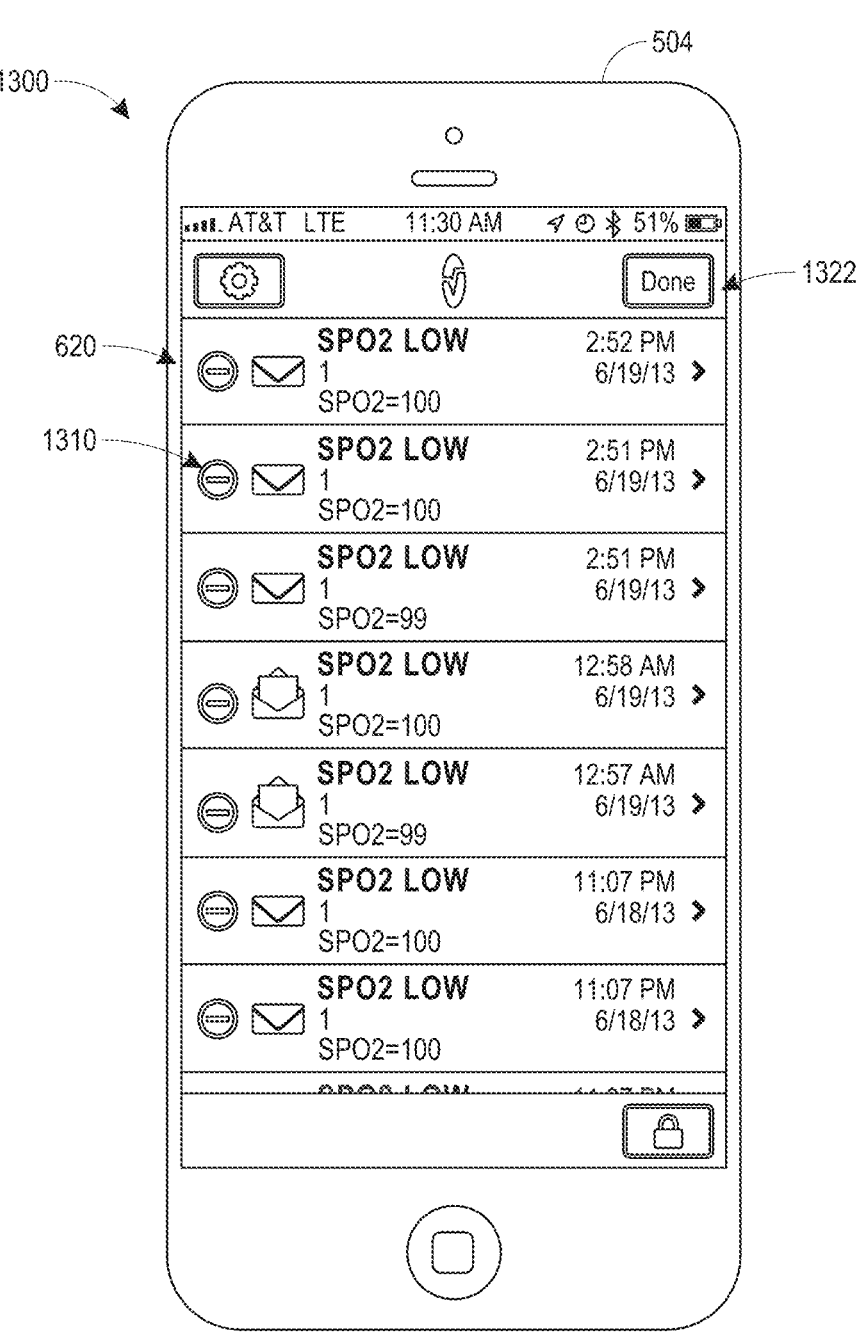

FIG. 13 depicts another user interface 1300 similar to the user interface 600 and 1200. The user interface 1300 may be accessed by selection of the edit button 622 in FIG. 6 or any of the previous screens that depicts the edit control 622. Selection of the edit control 622 can cause delete selector controls 1310 to be depicted next to the notifications 620.

Figure 14:
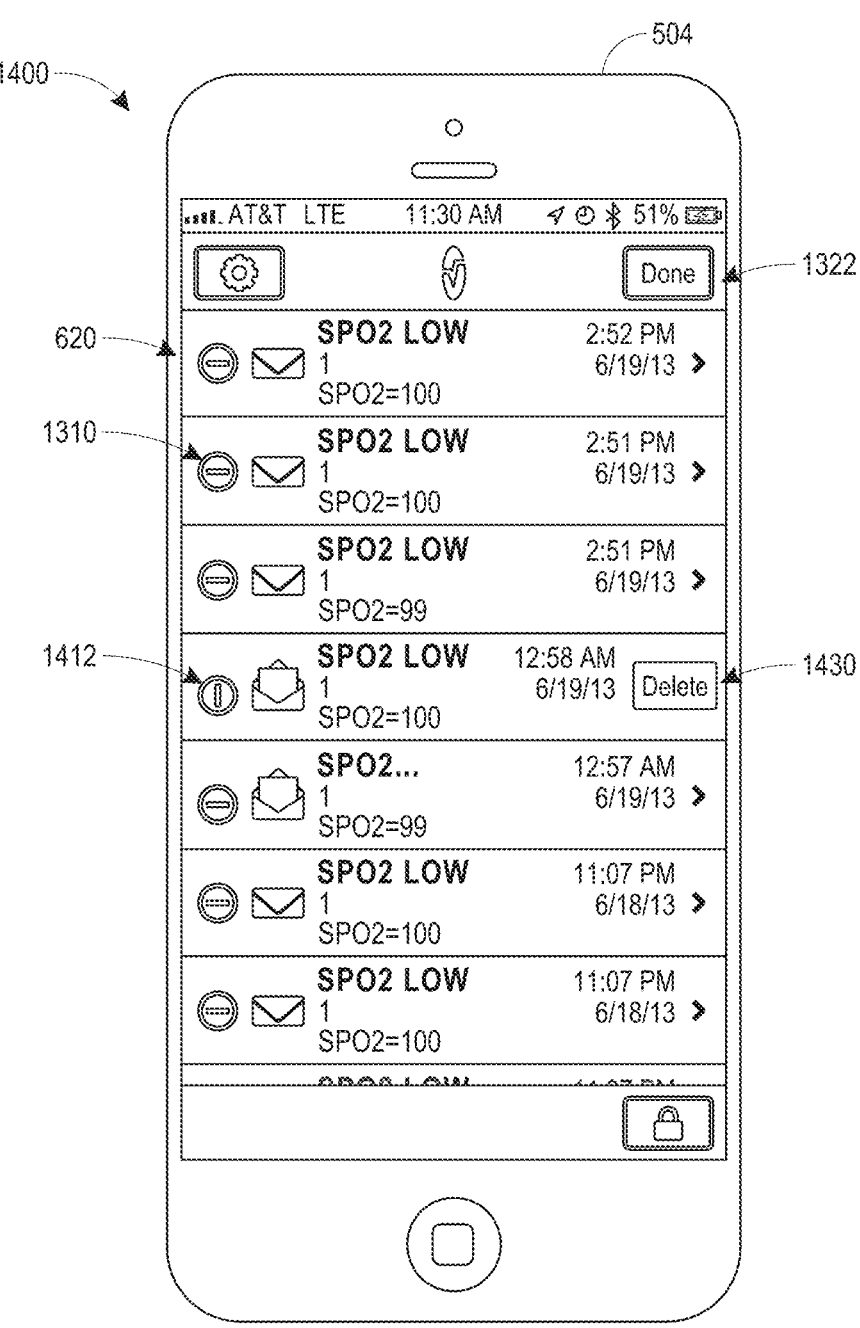

Selection of a deletion selector control 1310 can cause a user interface such as that shown in FIG. 14 to be displayed. The user interface 1400 includes a selected delete selector control 1412, which selection causes a delete button 1430 to be displayed in-line with the notification 620 selected for deletion. A user can select the delete button 1430 to cause the notification to be deleted and then select the done button 1322 to leave the edit view. Thus, in one embodiment, three user inputs are used (selecting the edit button, the delete selector control 1310, and then the delete button 1430) to delete a notification, thereby enabling deletions without having too few steps to make deletions too easy to accidentally perform. In other embodiments, however, there may be other mechanisms for deleting notification 620 such as long pressing to delete, swiping to delete, or the auto deletion scenario described above.

Figure 15:
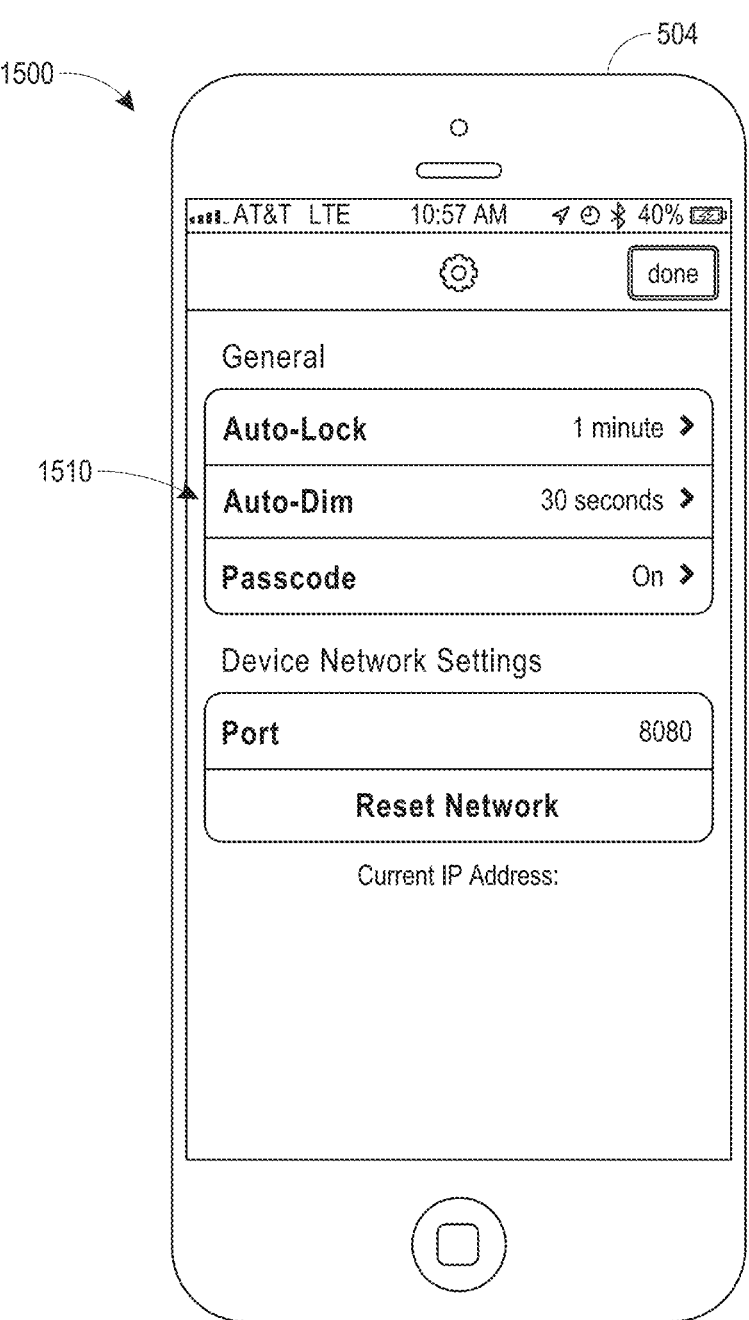

FIG. 15 depicts an example user interface 1500 that may be reached by selection of the settings control 620 from FIG. 6 and depicts various settings 1510 associated with an embodiment of the notification client 108. These settings 1510 include an auto-lock timer, an auto-dim timer, passcode function and network parameters such as a port for which to communicate with the MMS 310. Other settings may also be provided in other embodiments.

Figure 16:
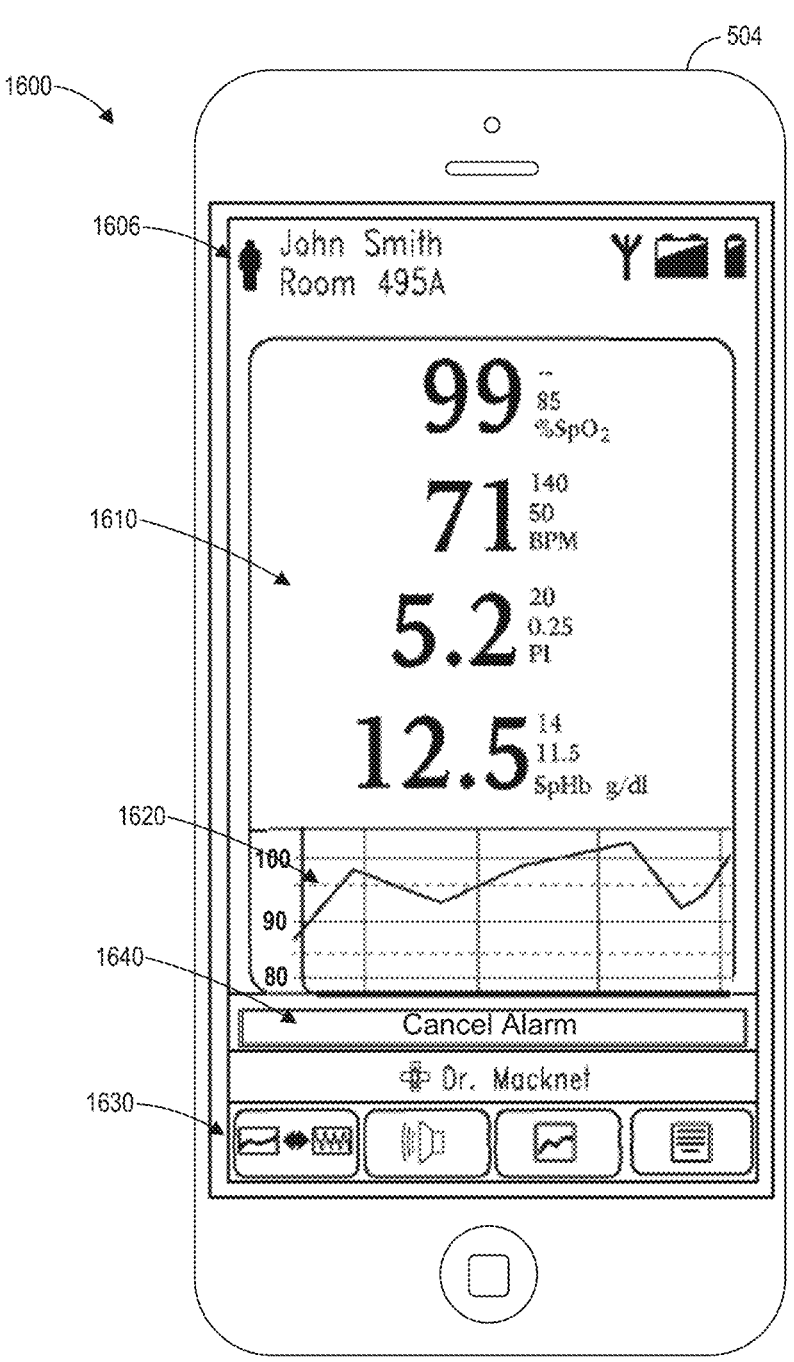

Turning to FIG. 16, another example user interface 1600 is shown that includes additional detailed patient information that may be accessed by selecting the additional details from any of the user interfaces described above or by other menu options not shown herein. The user interface 1600 includes patient biographical info 1606, parameter values 1610, and a parameter trend 1620 that depicts values of a selected parameter over time. The parameter trend 1620 can depict the parameter that triggered the alarm or another parameter and may be selected by the clinician. Although not shown, the wellness index described above or a trend thereof may also be shown.

One value of depicting the parameter trend 1620 and/or the parameter values 1610 in more detail can enable a clinician to determine whether the alarm is actionable. The parameter value 1610 and the trend 1620 can update as the clinician is observing the user interface 1600. Thus, the clinician can observe the parameter value 1610 and/or the trend 1620 to see if the patient comes out of the alarm state. As a result, the clinician may decide that the patient does not need intervention or perhaps that immediate intervention is not needed. The clinician can then use this information to prioritize other more serious alarms over this alarm.

In other embodiments, if the clinician determines that no intervention is necessary, the clinician can select a control 1640 to cancel the alarm remotely. In response to selection of the control 1640, the notification client 108 can send a message to the MMS 110, which sends an alarm cancellation message to the patient device 102.

The user interface 1600 also includes menu options 1630 to select between trend and parameter waveform views. In addition, the menu options 1630 can turn audio on or off. The audio may include audio obtained from a respiration sensor attached to the patient, which can detect the patient's breathing sounds. The audio may also include audio from a microphone attached to or coupled with the patient device 102, which can allow the clinician to communicate with the patient verbally. Video options are also available (see FIG. 17) for viewing a video of the patient. Video may include two-way video chat in an embodiment, such that the clinician device 504 captures video of the clinician and provides this video to the patient device (e.g., through the MMS or directly), which in turn outputs the video or outputs the video on a separate display, such as a television in the patient's room. The MMS can also route the video directly to a television or monitor in the patient's room. Through these audio and/or video features, the clinician can observe the health of the patient remotely, even while walking toward the patient's room to clear the alarm. The clinician can therefore anticipate in advance, based on what he or she sees and/or hears, what needs the patient may have, enabling the clinician to call for additional help, equipment, or medicines as necessary. Accordingly, providing audio and/or video of the patient to the clinician device can enable clinicians to improve patient outcomes.

In another embodiment, the user interface 1600 can be modified to depict the same user interface that is shown on the patient device, enabling the clinician to see exactly or substantially the same type of view as if he or she were to enter into the patient's room and view the patient device in person. In another embodiment, the user interface 1600 can depict a view of a second screen monitor that receives other parameters being monitored for the patient, such as a television that receives ventilation data or other data.

Any of these audio, video, and screen-sharing features can facilitate the performance of telemedicine or remote monitoring of patients.

Further, in some embodiments, the options 1630 enable the clinician to annotate an alarm to include a note as to what the clinician thinks should be done. The clinician device can transmit this annotated note to the patient device (e.g., through the MMS), which can display the note. Thus, a second clinician who sees a note written by a first clinician may have the benefit of the first clinician's thinking on the alarm, even if the first clinician cannot personally remediate the alarm. Similarly, the options 1630 can allow the clinician to dictate a recommended course of action, which can be sent to the patient monitor and played back.

Figure 17:
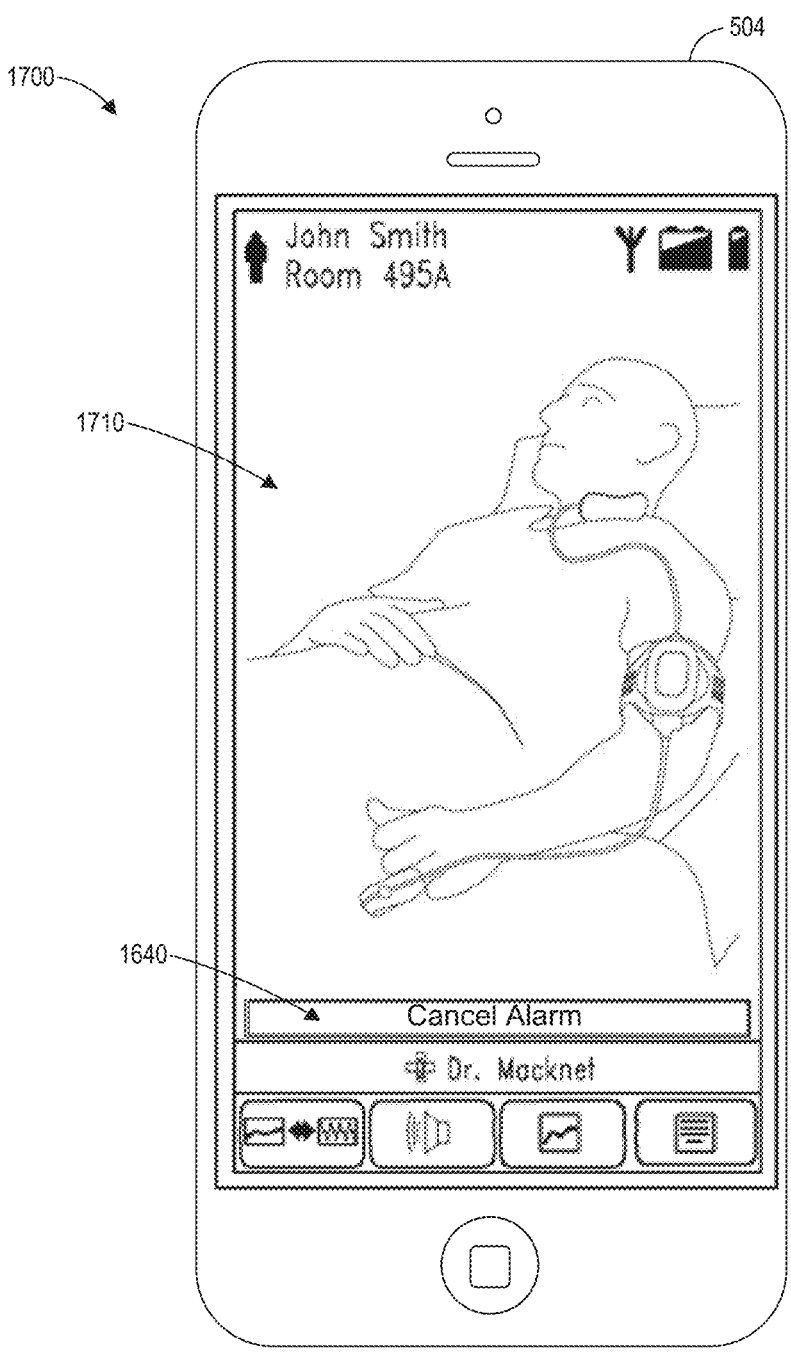

Turning to FIG. 17, another example user interface 1700 is shown, which depicts a video 1710 of the patient that may be obtained by a video camera installed on a patient device or other location in a patient's room. The video view can help the clinician determine the status of the patient and it may further facilitate the telemedicine features described above. If the clinician determines from the video 1710 that the patient is in suitable condition that would facilitate remediating the alarm, the clinician can select the cancel alarm button 614 as in FIG. 16 to remediate the alarm.

VI. Patient Admit Embodiments

Figure 18:
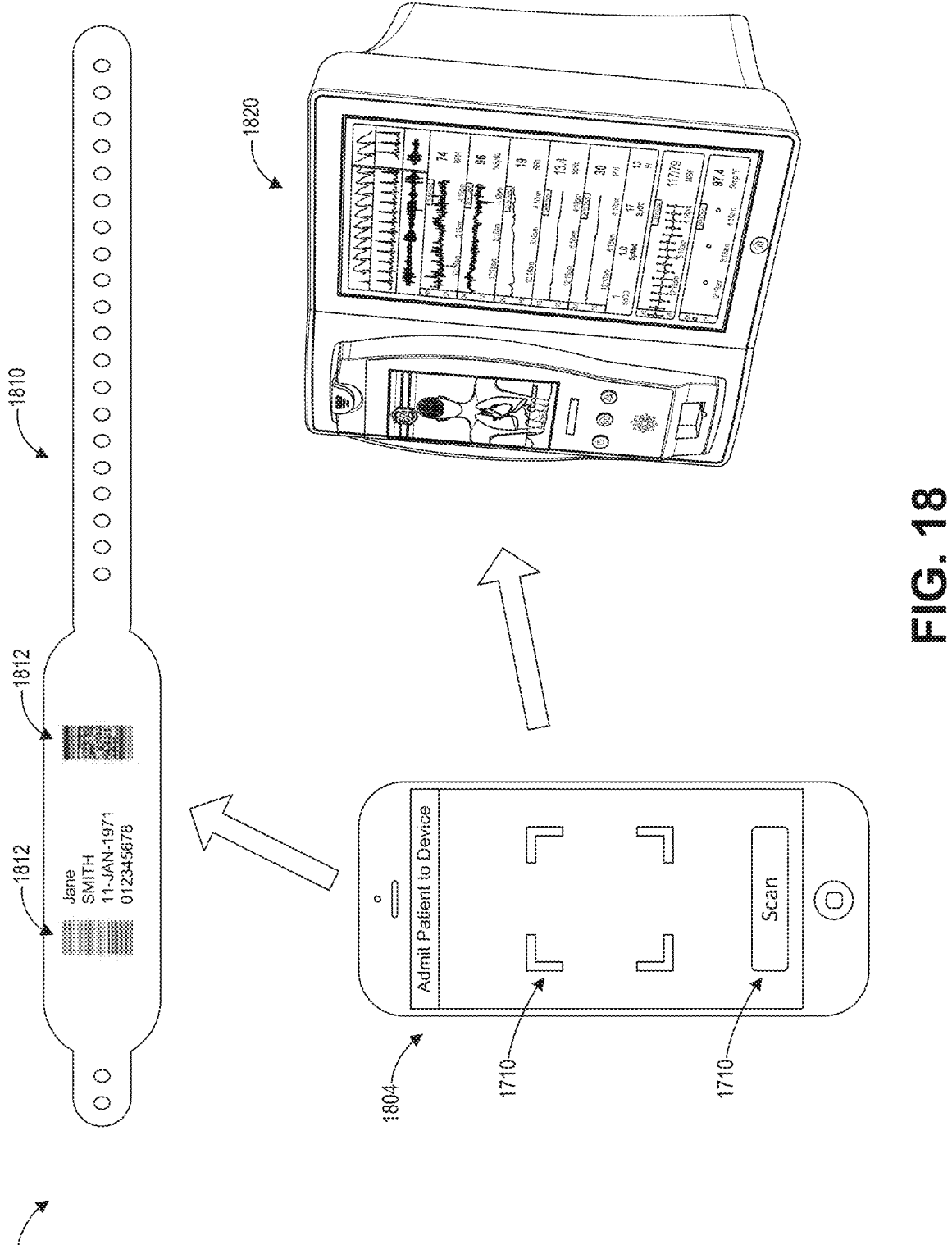
FIG. 18 depicts an example scenario for admitting a patient to a device or location.

Turning to FIG. 18, an example scenario 1800 is shown for admitting a patient to a device. In the scenario 1800, as described above with respect to the admit module 226 of FIG. 2, it can be desirable to automatically associate a patient with a device so as to reduce or eliminate errors that can occur through typing such information into a computer. Automatic patient-device association can also speed up the care of a patient by quickly facilitating the association of the patient with the device.

Admitting that patient to a device is distinct from admitting a patient to a hospital in one embodiment, although these two separate activities may in practice occur at the same time. In one embodiment, the patient is first admitted to the hospital, and during this process, information about the patient is stored in the MMS 110 or EMR 120. Subsequently, the patient may be assigned a room in the hospital and/or a patient device 102 (see FIG. 1) to monitor that patient. The patient may be admitted to the patient device so as to associate a profile of the patient in the MMS 110 with the patient device. Admitting the patient to the device can enable accurate tracking of the patient's movements through the hospital, accurate keeping of records in an electronic medical record (EMR) system associated with the MMS 110, accurate escalation of alarms with accurate patient data, as well as possibly other benefits.

In the depicted embodiment, a clinician device 1804 is shown that can include all the features of the clinician devices described herein. The clinician device 1804 can include the functionality of the admit module 112 or 226 described above with respect to FIGS. 1 and 2 and may, for instance, include the ability to scan machine readable codes, RFID tags, or the like. For instance, the clinician device 1804 includes a scanner view 1710 that enables a user to scan machine readable codes and a scan button 1710 that enables the user to select the scan button 1710 to cause the scan to occur by the clinician device 1804. In alternative embodiments, the clinician device 1804 does not include the scan button 1710 but instead automatically scans any image that it encounters and then determines whether the image includes a machine readable code. The scanner can automatically extract the information from the machine readable code accordingly.

A patient bracelet 1810 is also shown which includes barcodes 1812 that can be scanned by the clinician device 1804. Although two barcodes 1812 are shown in this example, one may be omitted in some embodiments. The two barcodes 1812 may be used for different purposes. A patient device 1820 is also shown that may also include a barcode that may be scanned by the clinician device 1804. In an embodiment, a clinician uses the clinician device 1804 to scan the patient bracelet 1810 and the patient device 1820 so as to associate the two together in physical computer storage. The clinician can scan the bracelet 1810 first or the device 1820 first. The clinician device 1804 can send data obtained from the scanned codes to the MMS so that the admit module 226 of the MMS can link together the device 1820 and the patient in computer storage. This linkage can enable the patient device 1820 to send data records associated with the patient to the EMR 120.

In other embodiments, instead of linking the patient bracelet 1810 with a patient device 1820, the clinician device 1804 can link the patient bracelet 1810 with a data record in the EMR 120 or MMS 110 that represents a location. Examples of such locations include a room, facility, bed, bassinette, or any other location in a clinical facility. As the patient is moved from room to room in a clinical facility, the clinician can use the clinician device 1804 to scan an identifier tag in or near or otherwise associated with (e.g., as a tag at the nurse's station) the new location (or new device in the new location). As a result, accurate records can be maintained for the patient and accurate alarm notifications may be sent, as described above.

In still other embodiments, the clinician device 1804 can use other technologies to automatically associate the patient bracelet 1810 with the patient device 1820 or patient location. For instance, the clinician device 1804 can scan an RFID tag in the patient bracelet 1810 and scan an RFID tag in the patient device 1820 or location associated with the patient so as to link the two together. Thus, more generally, the clinician device 1804 can scan identifier tags and cause the identifiers of those tags to be associated together.

Thus, the patient bracelet 1810 is an example of an identification tag that can be scanned optically (if including a machine-readable code such as a barcode) or wirelessly (e.g., if the bracelet 1810 includes an RFID tag). Similarly, a sticker or plate affixed to the patient device 1820 or location is also an example of an identification tag that can be scanned optically (if including a machine-readable code such as a barcode) or wirelessly (e.g., if the bracelet 1810 includes an RFID tag).

Figure 19:
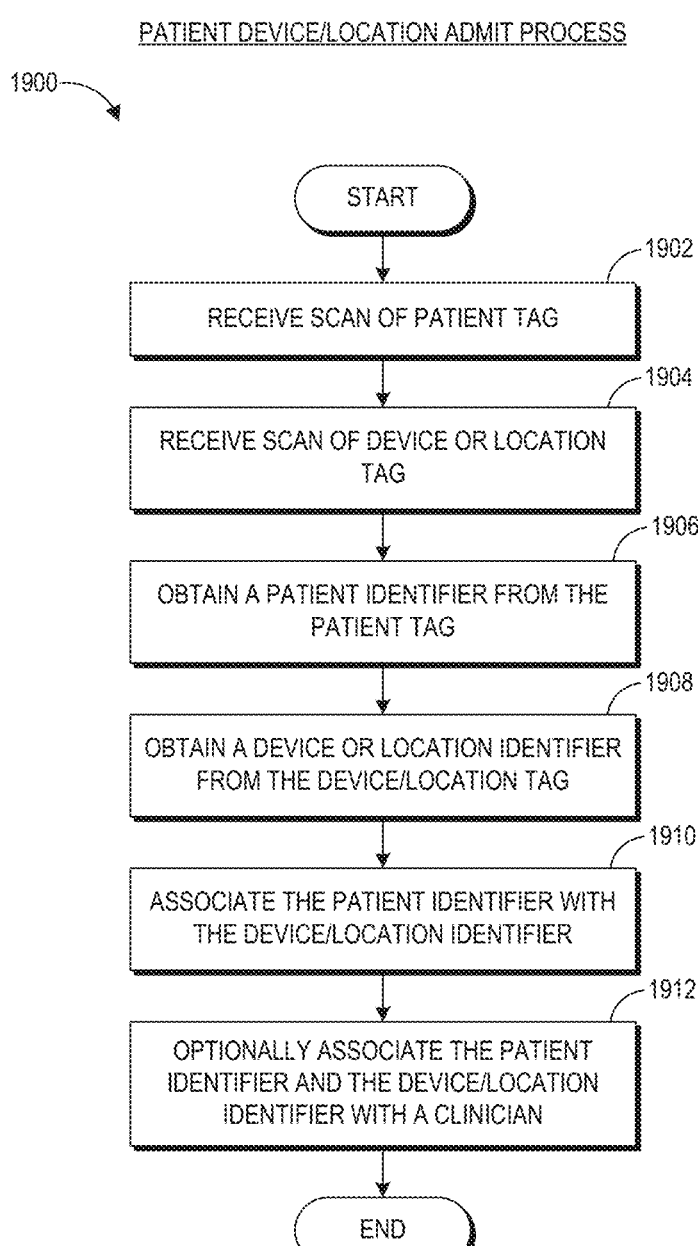
FIG. 19 depicts an example process for admitting a patient to a device or location.

FIG. 19 depicts an example process 1900 for associating a patient with a device or location. The process 1900 may be implemented by any of the systems or devices described herein. For convenience, the process 1900 will be described in the context of the clinician device, although other computing devices not described herein may implement the process 1900.

At block 1902, the clinician device receives a scan of a patient tag which may be an RFID tag, machine readable code or the like. At block 1904, the clinician device receives a scan of a device or location tag and obtains a patient identifier from the patient tag at block 1906. The clinician device obtains a device or location identifier from the device or location tag at block 1908.

The clinician device associates the patient identifier with the device or location identifier 1910 in an embodiment, for instance, by providing both of these identifiers to the admit module 226 described above with respect to FIG. 2. The admit module 226 can in turn store an association between the device or location and the patient in the EMR 120. At block 1912, the clinician device can optionally associate the patient identifier in the device or location identifier with a clinician, such as the clinician who is the user of the clinician device. As a result, in an embodiment, the MMS can know which clinician is assigned to the patient and which patient device is assigned to the patient programmatically.

Figure 20:
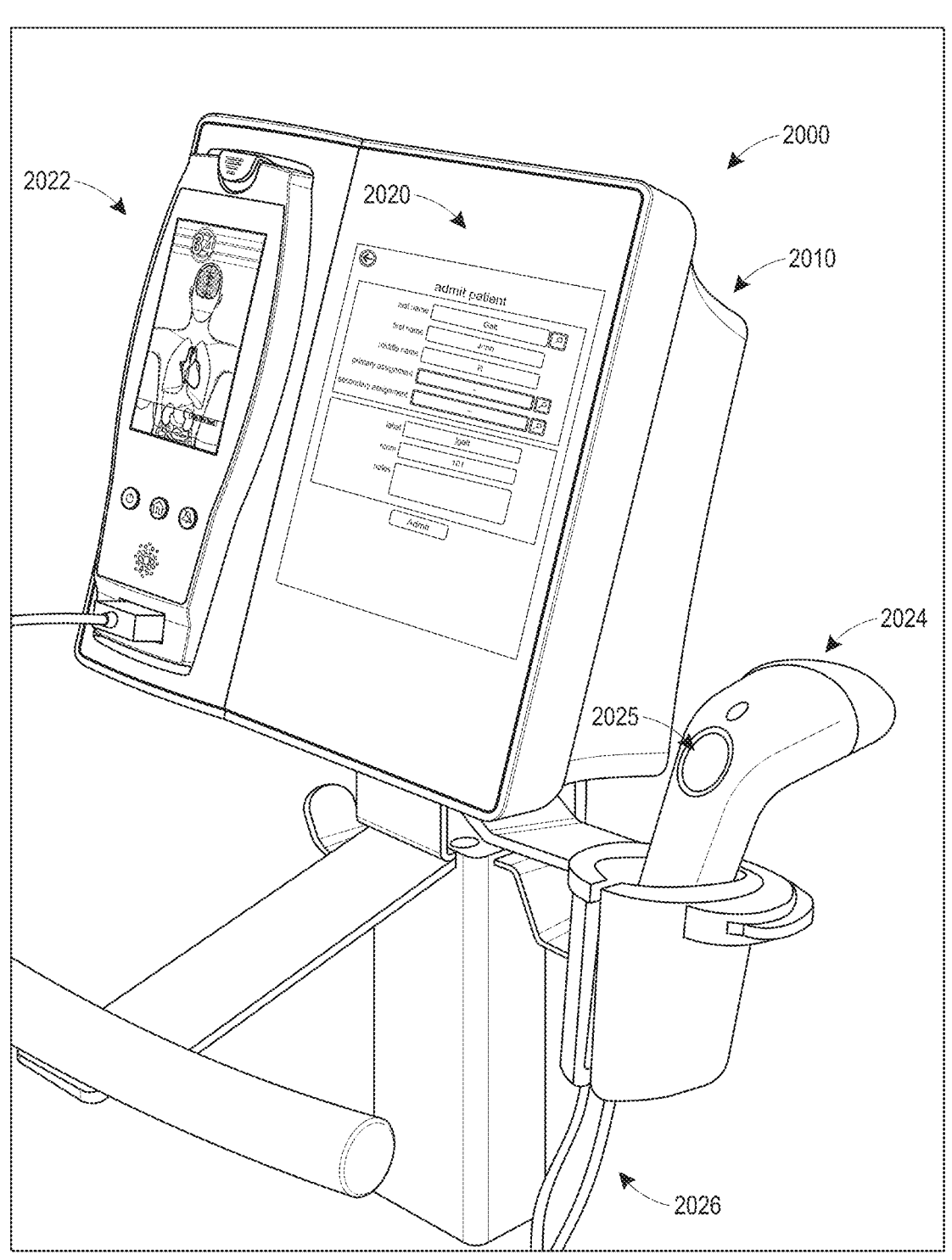
FIG. 20 depicts an embodiment of a patient monitoring device with a scanner for admitting the patient to the device.

FIG. 20 depicts an embodiment of a patient monitoring device 2000 with a scanner 2024 for admitting the patient to the device. The patient monitoring device 2000 is another example of the monitoring device 1820 and may include all the features thereof. Likewise, the patient monitoring device 2000 is an example of the patient devices 102 described above. The patient monitoring device 2000 includes a hub 2010 (which is an example of a patient monitor) and a portable physiological monitor (PPM) 2022. The PPM 2022 is also an example patient device 102 and connects to the hub 2010 via a docking port (obscured by the connection of the PPM 2022 to the hub 2010). The hub 2010 and PPM 2022 may have all the functionality of the corresponding hubs and PPMs described in U.S. application Ser. No. 13/651,167, titled "Medical Monitoring Hub," filed Oct. 12, 2012, the disclosure of which is hereby incorporated by reference in its entirety. For instance, physiological parameter data may be output on a display 2020 of the hub 2010 and/or on a display of the PPM 2022. In addition to their ordinary meaning, this specification often uses the terms "physiological monitor," "patient monitor," and "patient device" interchangeably.

In the embodiment shown, the display 2020 of the hub 2010 includes a patient admit screen that may implement some or all of the functionality described above with respect FIGS. 18 and 19. Additional examples of patient admit user interfaces are described in greater detail below with respect to FIGS. 21 through 25. The scanner 2024 shown is an example of an optical scanner that can be used instead of the clinician device 1804 to scan the identifier tags described above with respect to FIG. 18. The scanner 2024 can include electrical circuitry and/or a processor configured to cause an infrared beam to be emitted, such that when the user brings the scanner 2024 into close proximity with an identifier tag, the scanner 2024 reads a value associated with the identifier tag. A button 2025 on the scanner 2024 may be depressed by a user to cause a scan to occur. In another embodiment, the scanner 2024 is an RFID scanner, rather than an optical scanner, and may have suitable circuitry configured to scan an RFID identifier tag. A cable 2026 connects the scanner 2024 to the hub 2010 to convey scanned data to the hub 2010 (or the PPM 2010) so that the hub can perform the admit processing described above, including with respect to FIG. 19. The scanner 2024 may be wireless in other embodiments.

Figure 21:
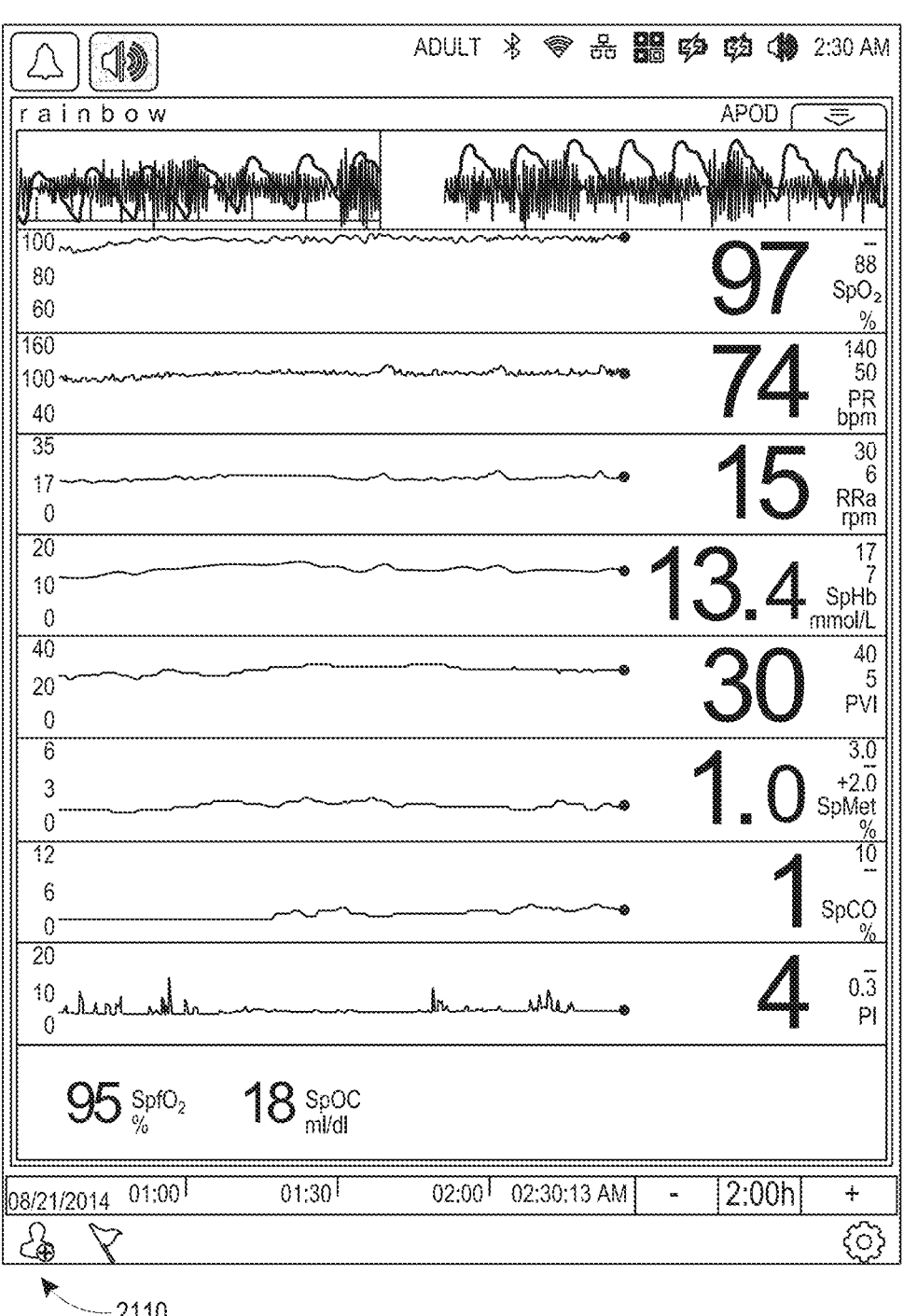
FIG. 21 depicts an example monitoring device user interface that includes functionality for initiating a patient admittance process.

FIG. 21 depicts an example monitoring device user interface that includes functionality for initiating a patient admittance process. The user interface can be implemented by any of the patient devices described herein, including patient devices 102, 1820, or 2000. The user interface shown in FIG. 21 displays numerous monitored physiological parameters of a patient. In addition, and admit icon 2110 is displayed. When pressed or otherwise selected (e.g., with a mouse) by a user (such as a clinician), the user can admit a patient to the patient device. Selecting the admit icon 2110 can enable a user to perform the scanning described above with respect to FIGS. 18 through 20. In another embodiment, selecting the admit icon 2110 can enable a user to perform a manual admit process without using the scanning technology described above.

FIGS. 22 through 25 depicts an example monitoring device user interface for admitting a patient to the device. These user interfaces can be implemented by any of the patient devices described herein, including patient devices 102, 1820, or 2000.

Figure 22:
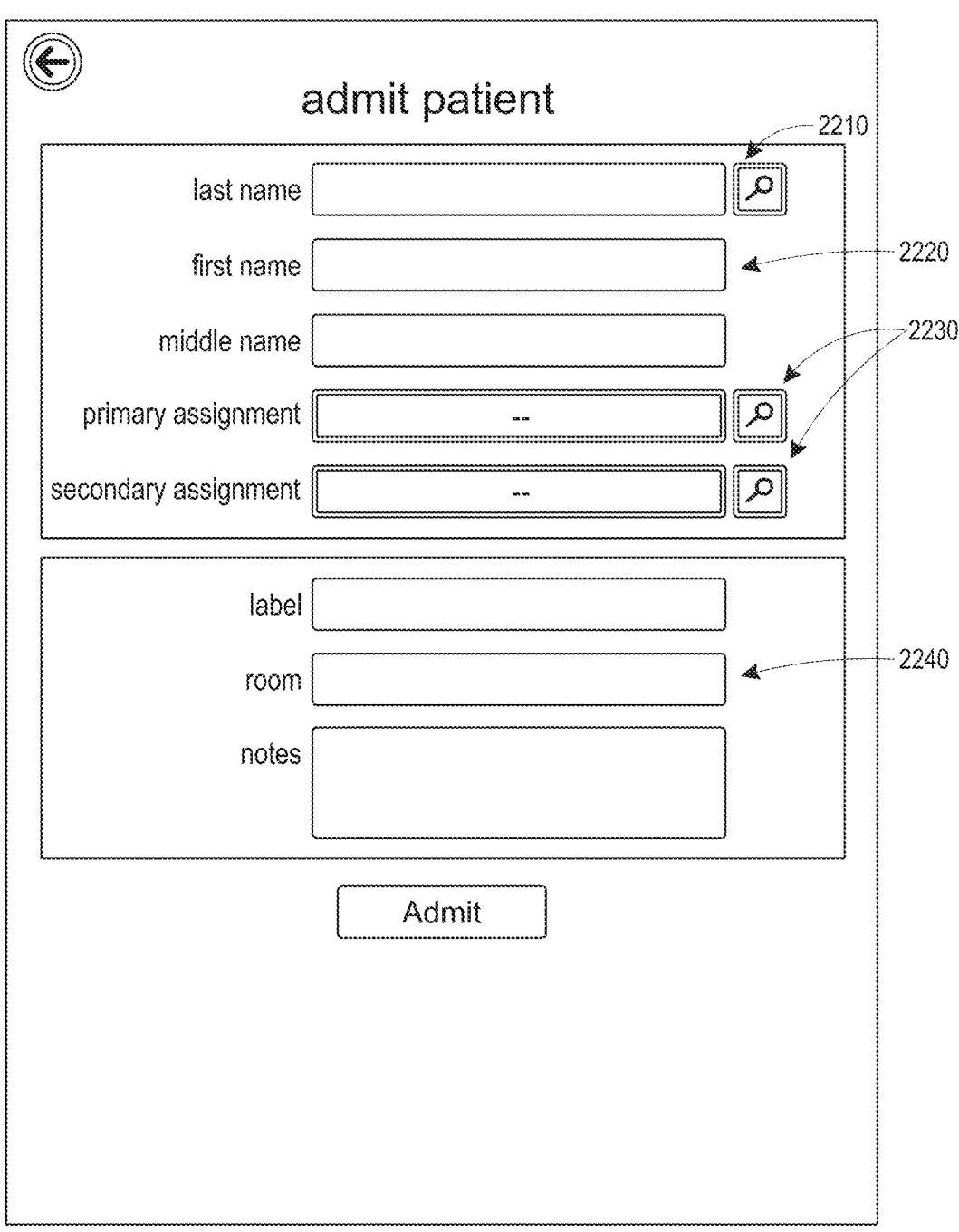

Referring specifically to FIG. 22, a user interface is shown that may be displayed by the patient device in response to the user selecting the admit icon 2110 of FIG. 21. The user interface shown includes a search button 2210 to enable a user to search for a patient's record (or the name of the patient) in the MMS 110 or EMR 120 (see FIG. 1). When the patient is admitted to the hospital, or at an earlier time, a patient record may be created in the MMS 110 or EMR 110, which may subsequently be searched for at the patient device to associate that patient with the device. As an alternative (or additional feature) to searching, a user may type the text of the patient's last name into a text box of the user interface next to the search button 2210.

Fields 2220 are also included for manually inputting a patient's first name and middle name. Search boxes 2230 are also provided for entering a primary assignment and an optional secondary assignment. The primary assignment may refer to a clinician assigned to be the primary caregiver of the patient, while the secondary assignment can refer to a clinician assigned to be a secondary caregiver of the patient. The primary and secondary assignments can be used in part to manage patient escalation using any of the escalation features described above. For instance, an alarm generated by the patient device may initially be sent to a clinician device of the primary assignment and may subsequently be escalated to a clinician device of the secondary assignment.

Text boxes 2240 are also provided for inputting a label or short name for the patient, a room number associated with the room that the patient is staying in at the hospital or clinical facility, and any notes a clinician wishes to provide.

Figure 23:
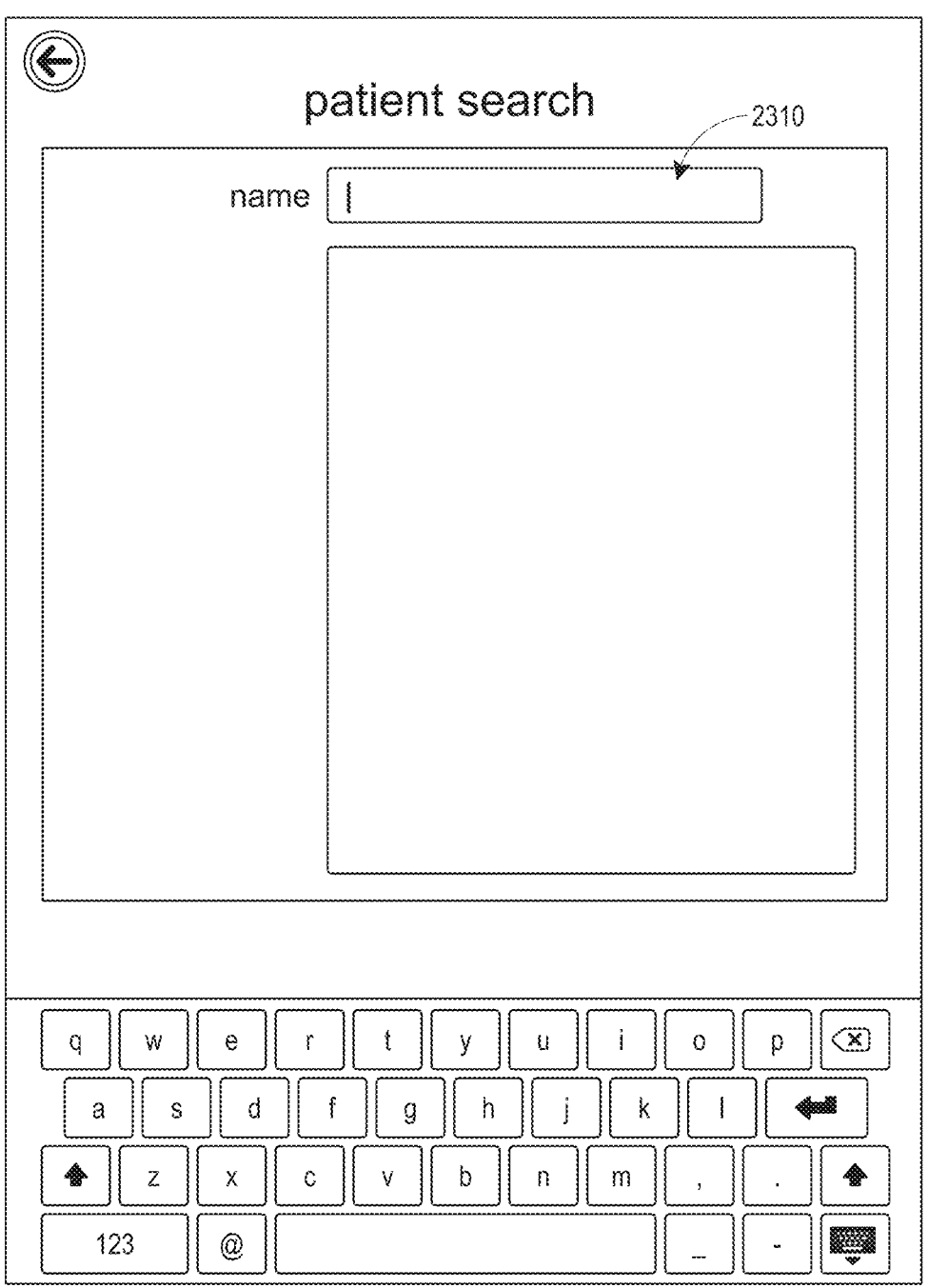
Figure 24:
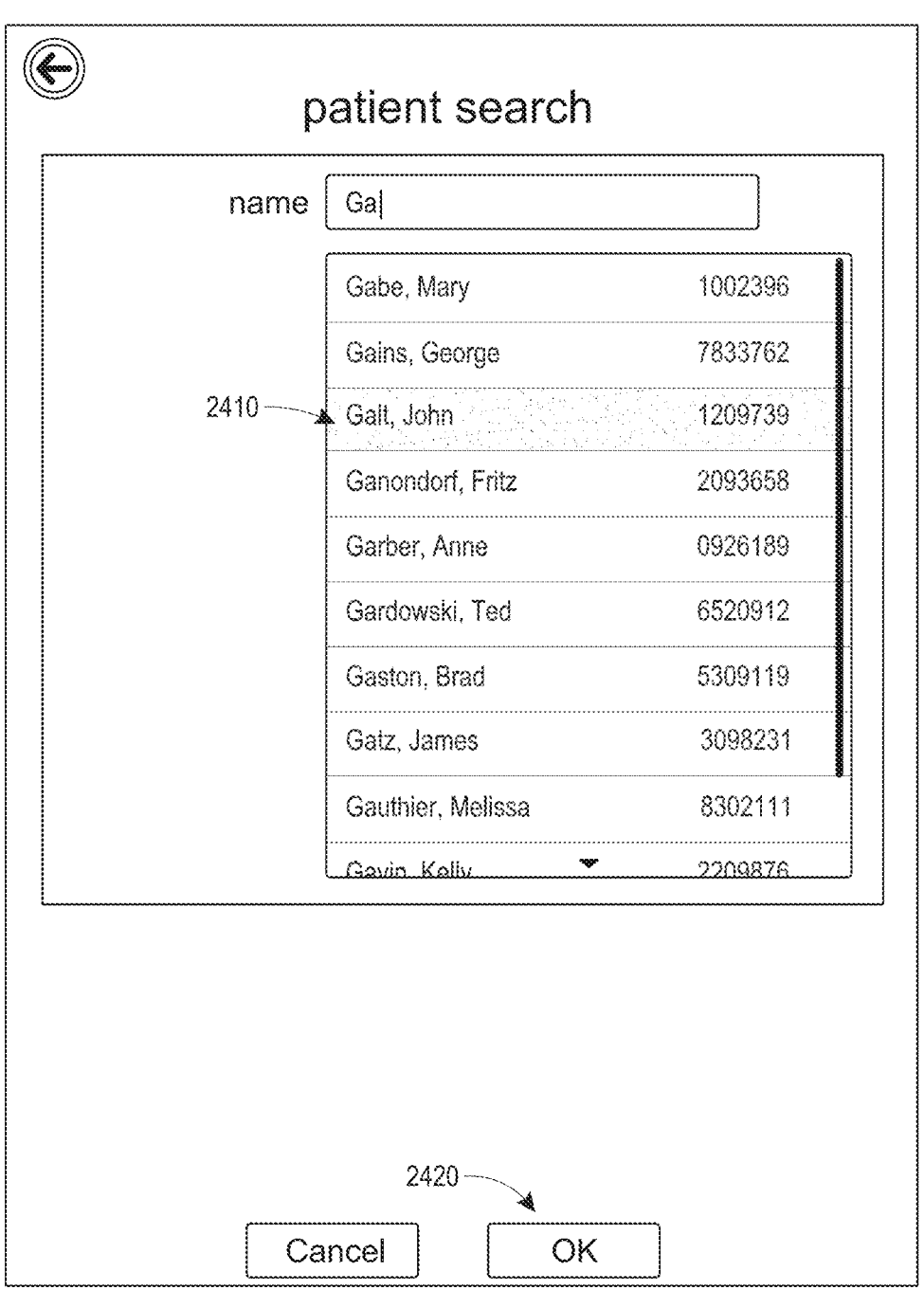

FIG. 23 depicts another example user interface with the text box 2310 for searching for patient. This user interface may be reached in an embodiment after a user selects the search button 2210 of FIG. 22. FIG. 24 shows another example user interface with example search results 2410 shown, which may be reached after the search is conducted in FIG. 23. The user can select a patient's name and touch an Okay button 2422 to continue the admit process.

FIG. 25 depicts a similar screen to FIG. 22, this time with patient name, label, and room number filled in. Any of this data may be populated automatically or manually as described above, based on the results of the search or based on user data entry. An admit button 2510 may be selected by the user to admit the user to the device. Upon selection of the admit button 2510 by a user, the patient device can send a notification or message to the MMS 110, which can store an identifier of the device together with the record of the patient in data storage, such as the EMR 120.

VII. Vital Signs Verification and Submission Embodiments

Periodically, nurses in a clinical facility read a patient's vitals and write those vitals down in a patient's chart, walk to the nurse's station, and input those vitals into computer to be associated with an electronic medical record of the patient. Examples of vitals that may be monitored by the nurse and written down include temperature, pulse, respiration, blood pressure, oxygen saturation, pain assessment, and level of consciousness (see also FIG. 27). Intervals for entering patient vitals may vary based on different monitoring situations and in different clinical facilities. One example interval would be to enter a patient's vitals half an hour after the patient has been admitted, and once every hour for four hours, and then once every 6 to 8 hours once the patient has stabilized.

Writing down vitals on a chart and physically entering the vitals into the computer can be time intensive and inaccurate. The patient devices described above can automatically send many vital signs to the electronic medical record of the patient associated with the MMS 110, but other vital signs are not continuously monitored by the patient devices. Thus, clinicians typically still enter such vital signs manually on paper in the process outlined above. An alternative approach is described below with respect to FIGS. 26 through 28.

Figure 26:
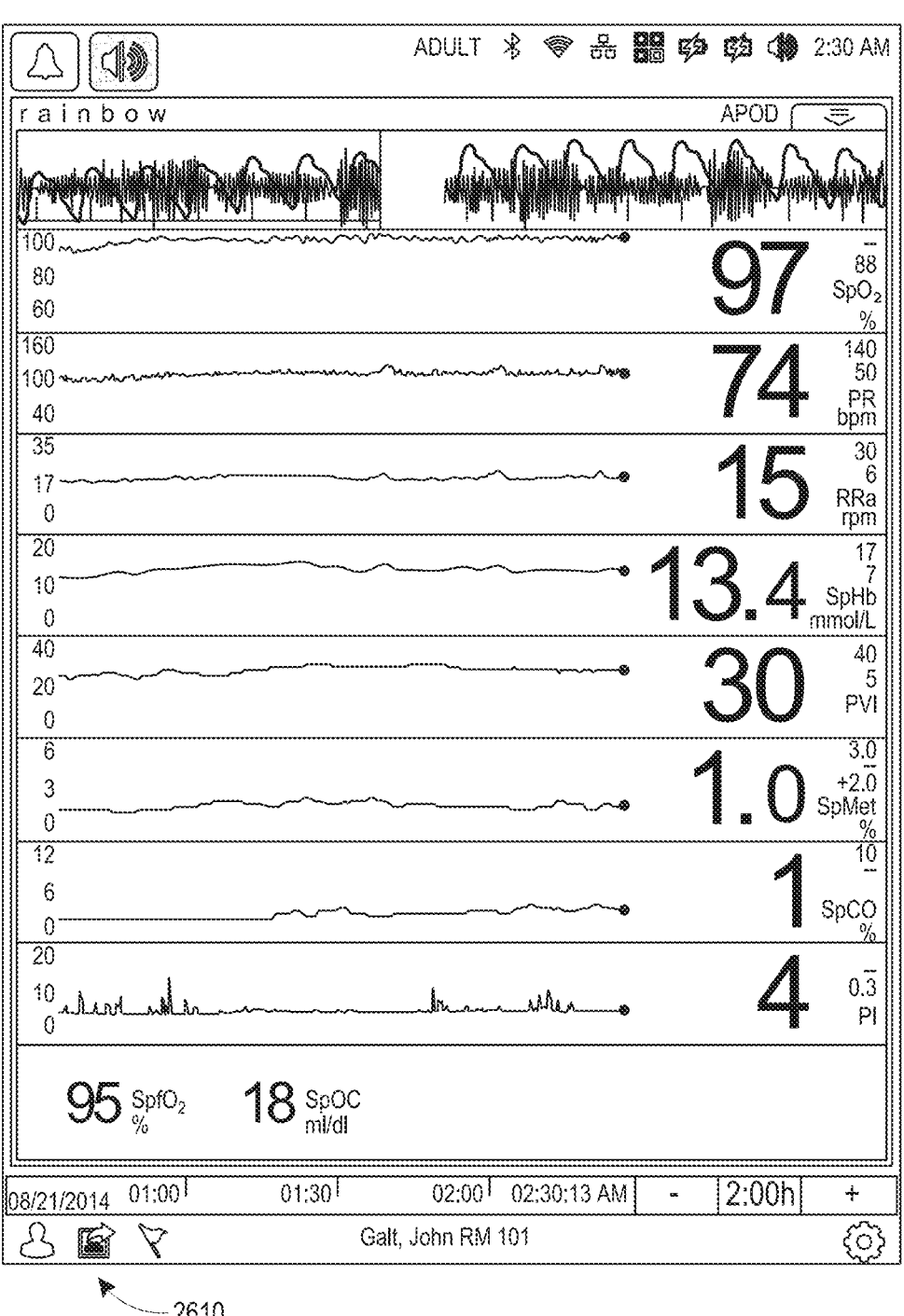
FIG. 26 depicts an example monitoring device user interface that includes functionality for initiating a vital signs submission process for an admitted patient.
Figure 27:
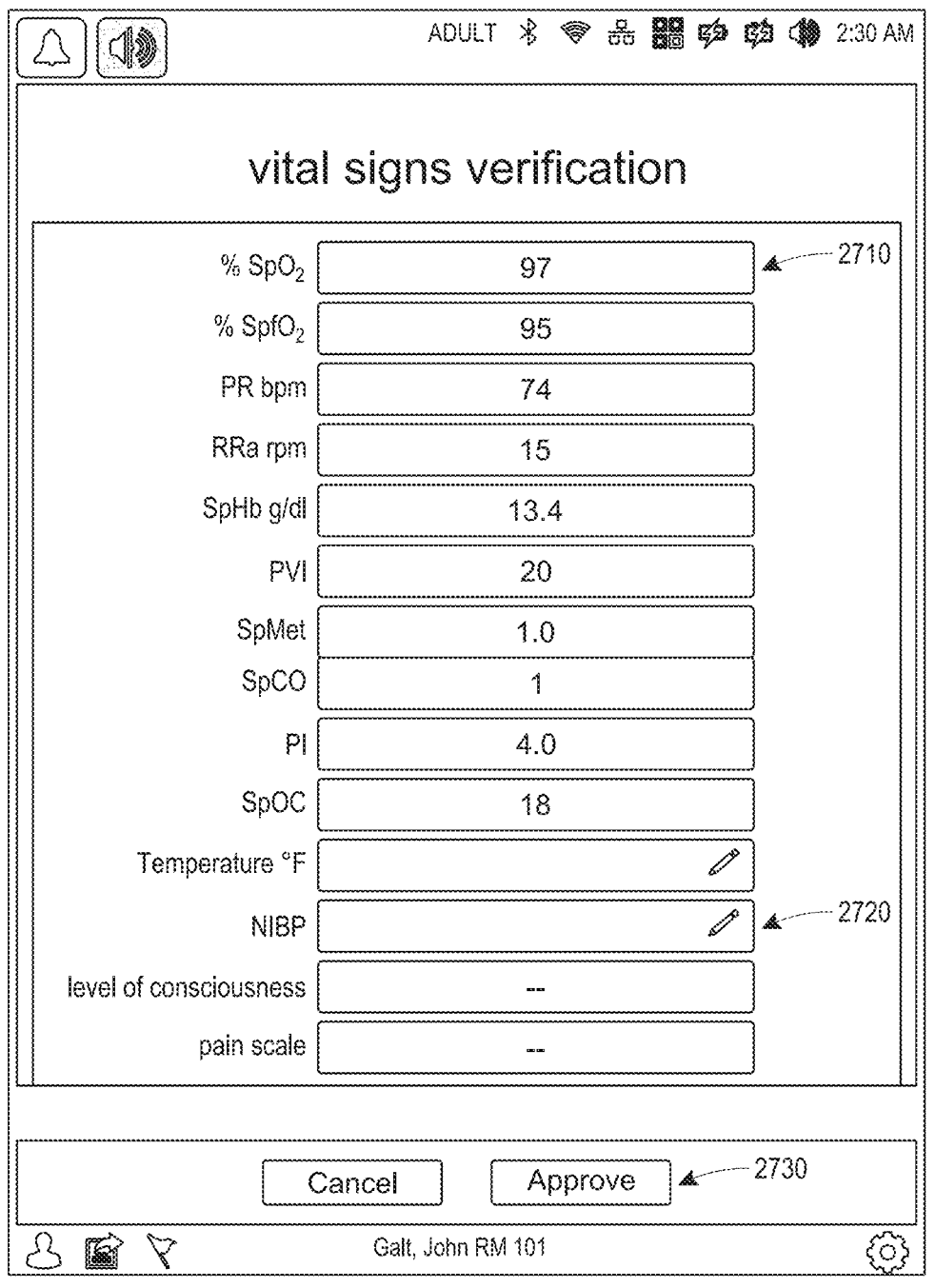
FIG. 27 depicts an example monitoring device user interface that includes functionality for submitting vital signs.
Figure 28:
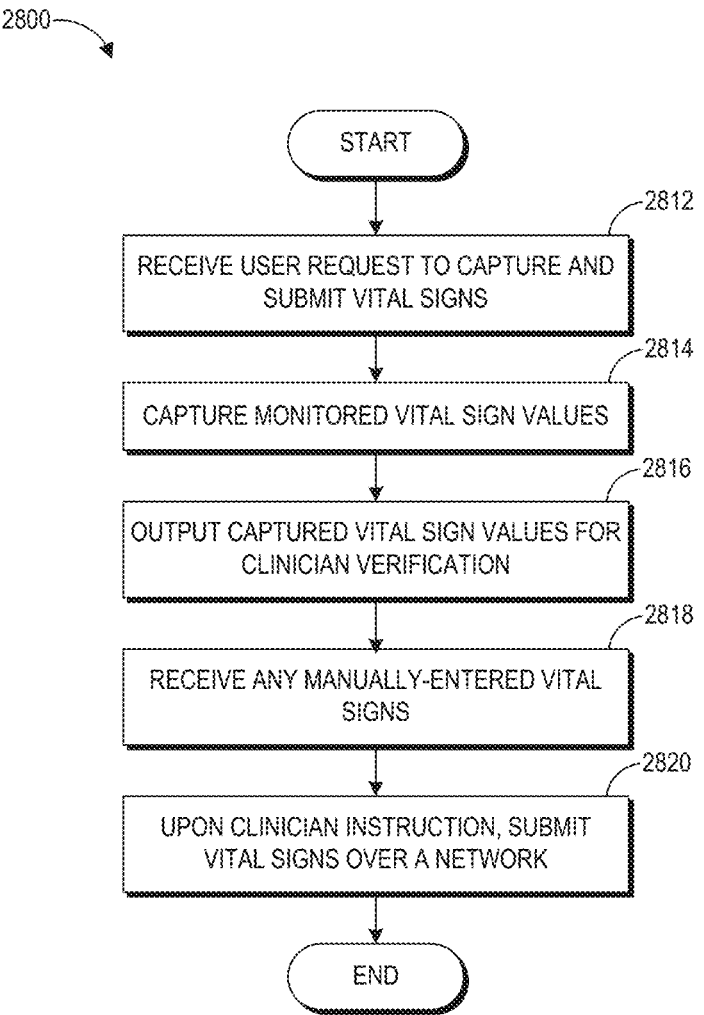
FIG. 28 depicts an embodiment of a process for verifying vital signs.

The approaches described with respect to FIGS. 26 to 28 may be implemented with an admitted patient or non-admitted patient, although doing so with an admitted patient may provide the advantage of simplifying the process of associating the vital signs with the correct patient record. Alternatively, vital signs may be submitted and later associated with a patient record (e.g., at the nurse's station or after the patient is admitted to the device). Both the automatic scanning or manually-inputted admit processes may be used prior to or after the vital signs verification and submission embodiments described below. The following embodiments can be implemented at least in part by the vital signs verification component 114 (see FIG. 1).

FIG. 26 depicts an example monitoring device user interface that includes functionality for initiating a vital signs submission process for an admitted patient. Once a patient has been admitted, vital signs can be captured by the patient device and/or by the clinician and submitted via the patient device to the MMS 110 for inclusion in the patient's electronic medical record. An icon 2610 in the user interface can be selected by a user to initiate a vitals verification and submission process.

Selection of the icon 2610 can cause a user interface such as the one shown in FIG. 27 to be displayed on the patient device. In particular, FIG. 27 depicts an example monitoring device user interface that includes functionality for submitting vital signs. Some vital signs 2710 are automatically captured by the patient device at the point in time that the user selects the icon 2610. Fields 2720 are provided for a user to optionally input additional vital signs not continuously monitored, including temperature, blood pressure (or noninvasive blood pressure (NIBP)), level of consciousness, and a pain scale rating. Each of the fields 2720 may be drop-down boxes or text boxes that the user can enter text or scroll down to select a value. Other fields for other spot-check sensor values or other patient parameter data, not shown, may also be displayed in other embodiments.

The level of consciousness values may include qualitative measures of consciousness, such as on a scale including alert, drowsy, lethargic, obtunded, and coma. Other scales may also be used. The pain scale may be a 1 to 10 pain scale rating, where 10 is the most severe pain and 1 is the least severe or zero pain. Other scales may also be used. A nurse can observe the level of consciousness campaign level and input the same in the fields 2720 with or without input from the patient.

An approved button 2730 is provided and may be selected by the user to submit the vital signs to the MMS 110 for inclusion in the EMR 120.

FIG. 28 depicts an embodiment of a process 2800 for verifying vital signs. The process 2800 may be implemented by any of the patient devices described above, including the patient device 102, 1820, or 2000. The process 2800 can cause the user interfaces described above with respect to FIGS. 26 and 27 to be output for display. Corresponding user input can be received in those user interfaces and can be sent to the MMS 110 as described above.

At block 2812, the patient device receives a user request to capture and submit vital signs. For instance, the user may select the icon 2610 in the user interface of FIG. 26 to initiate the vital signs verification and submission process. At block 2814, the patient device automatically captures monitored vital sign values at that point in time (e.g., from a most recent or recent value stored in a memory device of the patient monitor). The patient device outputs the captured vital sign values for clinician verification at block 2816. An example display including such values is described above with respect to FIG. 27.

At block 2818, the patient device receives any manually entered vital signs. Such manually entered vital signs may be implemented using the user interface of FIG. 27 or the like. Upon clinician instruction (such as by selection of the Okay button 2730 of FIG. 27), the patient device submits the vital signs over a network (e.g., to the MMS 110) at block 2820.

VIII. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

Each of the user interfaces shown includes one or more user interface controls that can be selected by a user, for example, using a browser or other application software associated with a patient or clinician device. The user interface controls shown are merely illustrative examples and can be varied in other embodiments. For instance, buttons, icons, dropdown boxes, select boxes, text boxes, check boxes, slider controls, and other user interface controls shown may be substituted with other types of user interface controls that provide the same or similar functionality. Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input, or keyboard input, among other user interface input options.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method of managing alarm notifications at a patient monitoring computing device, the method comprising:
sending an alarm notification message to a user device associated with a user;
determining whether a first indication that the alarm notification message was received by the user device has been received from the user device; and
in response to receiving, from the user device, the first indication:
determining whether a second indication that the alarm notification message was viewed by the user at the user device has been received from the user device, wherein the second indication indicates that the user has viewed but not yet responded to the alarm notification message; and
in response to receiving, from the user device, the second indication:
determining whether a response responsive to an input that the user has declined handling an alarm has been received from the user device; and
in response to receiving, from the user device, the response responsive to the input, accelerating escalation of the alarm.

2. The method of claim 1 further comprising:
in response to not receiving, from the user device, the first indication, accelerating escalation of the alarm.

3. The method of claim 1 further comprising:
in response to not receiving, from the user device, the response responsive to the input:
determining whether the alarm has been cleared; and
in response to determining that the alarm has not been cleared, accelerating escalation of the alarm.

4. The method of claim 1 further comprising:
determining whether or not an escalation condition is present based at least in part on at least one of: receipt or non-receipt of the first indication from the user device, receipt or non-receipt of the second indication from the user device, or receipt or non-receipt of the response from the user device; and
in response to determining that the escalation condition is present, automatically escalating the alarm by sending the alarm notification message to a second user device associated with a second user.

5. The method of claim 1, wherein the input comprises an indication that the user has marked the alarm notification message as unread.

6. The method of claim 1, wherein the input comprises an indication that the user is unable to respond to the alarm.

7. The method of claim 1, wherein the user device comprises a smartphone or other mobile device.

8. The method of claim 1 further comprising:
sending the alarm notification message in response to receiving an alarm indication from a patient monitor.

9. The method of claim 8, wherein the patient monitor is configured to:
determine that physiological parameter values trigger an alarm; and
send, to the patient monitoring computing device, the alarm indication responsive to determining that the physiological parameter values trigger the alarm.

10. A system comprising:
physical computer hardware configured to:
send an alarm notification message to a user device associated with a user;

determine whether a first indication that the alarm notification message was received by the user device has been received from the user device; and in response to receiving, from the user device, the first indication:

determine whether a second indication that the alarm notification message was viewed by the user at the user device has been received from the user device, wherein the second indication indicates that the user has viewed but not yet responded to the alarm notification message; and in response to receiving, from the user device, the second indication:

determine whether a response responsive to an input that the user has declined handling an alarm has been received from the user device; and in response to receiving, from the user device, the response responsive to the input, accelerate escalation of the alarm.

11. The system of claim 10, wherein the physical computer hardware is further configured to:

in response to not receiving, from the user device, the first indication, accelerate escalation of the alarm.

12. The system of claim 10, wherein the physical computer hardware is further configured to:

in response to not receiving, from the user device, the response responsive to the input:

determine whether the alarm has been cleared; and in response to determining that the alarm has not been cleared, accelerate escalation of the alarm.

13. The system of claim 10, wherein the physical computer hardware is further configured to:

determine whether or not an escalation condition is present based at least in part on at least one of: receipt or non-receipt of the first indication from the user device, receipt or non-receipt of the second indication from the user device, or receipt or non-receipt of the response from the user device; and in response to determining that the escalation condition is present, automatically escalate the alarm by sending the alarm notification message to a second user device associated with a second user.

14. The system of claim 10, wherein the input comprises an indication that the user has marked the alarm notification message as unread.

15. The system of claim 10, wherein the input comprises an indication that the user is unable to respond to the alarm.

16. The system of claim 10, wherein the user device comprises a smartphone or other mobile device.

17. The system of claim 10, wherein the physical computer hardware is further configured to:

send the alarm notification message in response to receiving an alarm indication from a patient monitor.

18. The system of claim 17, wherein the patient monitor is configured to:

determine that physiological parameter values trigger an alarm; and send, to a patient monitoring computing device of the system, the alarm indication responsive to determining that the physiological parameter values trigger the alarm.

* * * * *